US009833427B2

(12) United States Patent
Miller et al.

(10) Patent No.: US 9,833,427 B2
(45) Date of Patent: Dec. 5, 2017

(54) CREATINE ESTER ANTI-INFLAMMATORY COMPOUNDS AND FORMULATIONS

(75) Inventors: Donald W. Miller, Winnipeg (CA); Samuel C. Augustine, Omaha, NE (US); Jon C. Wagner, Omaha, NE (US); Thomas L. McDonald, Omaha, NE (US); Dennis H. Robinson, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 446 days.

(21) Appl. No.: 12/723,003

(22) Filed: Mar. 12, 2010

(65) Prior Publication Data

US 2011/0224174 A1  Sep. 15, 2011

Related U.S. Application Data

(63) Continuation of application No. 11/955,681, filed on Dec. 13, 2007, now abandoned, which is a continuation-in-part of application No. 10/365,666, filed on Feb. 12, 2003, now abandoned, which is a continuation-in-part of application No. PCT/US01/28788, filed on Sep. 14, 2001.

(60) Provisional application No. 60/232,969, filed on Sep. 14, 2000.

(51) Int. Cl.
*A01N 57/00* (2006.01)
*A61K 31/66* (2006.01)
*A61K 31/22* (2006.01)

(52) U.S. Cl.
CPC .............. *A61K 31/22* (2013.01); *A61K 31/66* (2013.01)

(58) Field of Classification Search
USPC ......................................................... 514/115
See application file for complete search history.

(56) References Cited

U.S. PATENT DOCUMENTS

| 3,088,871 | A | | 5/1963 | Pfeiffer | |
|---|---|---|---|---|---|
| 4,647,453 | A | * | 3/1987 | Meisner | A61K 31/7004 424/49 |
| 5,576,316 | A | | 11/1996 | Cohn | |
| 5,643,943 | A | | 7/1997 | Gamache et al. | |
| 5,773,473 | A | | 6/1998 | Green et al. | |
| 5,976,547 | A | * | 11/1999 | Archer | A61K 9/0014 424/742 |
| 5,994,581 | A | | 11/1999 | Fang | |
| 6,093,746 | A | | 7/2000 | Uchida et al. | |
| 6,093,848 | A | | 7/2000 | Greindl et al. | |
| 6,117,872 | A | | 9/2000 | Maxwell et al. | |
| 6,136,339 | A | * | 10/2000 | Gardiner | 424/439 |
| 6,242,490 | B1 | | 6/2001 | Anelli et al. | |
| 6,242,491 | B1 | | 6/2001 | Kaddurah-Daouk | |
| 6,413,552 | B1 | * | 7/2002 | Stoll | A61K 9/0014 424/497 |
| 6,503,951 | B2 | | 1/2003 | Pischel et al. | |
| 6,730,331 | B1 | * | 5/2004 | Stoll | A61K 9/0014 424/497 |
| 6,897,334 | B2 | | 5/2005 | Vennerstrom | |
| 2002/0049253 | A1 | | 4/2002 | Kaddurah-Daouk | |
| 2003/0212130 | A1 | | 11/2003 | Miller et al. | |
| 2003/0212136 | A1 | | 11/2003 | Vennerstrom et al. | |
| 2004/0029969 | A1 | * | 2/2004 | Blatt | A61K 8/44 514/565 |
| 2004/0077719 | A1 | | 4/2004 | Jager et al. | |
| 2004/0242691 | A1 | | 12/2004 | Miller et al. | |
| 2007/0203076 | A1 | | 8/2007 | Vennerstrom et al. | |

FOREIGN PATENT DOCUMENTS

| GB | 1185882 | 3/1970 |
|---|---|---|
| WO | 9633707 | 10/1996 |
| WO | 0010408 | 3/2000 |
| WO | WO 0222135 A1 * | 3/2002 |
| WO | 02058488 | 8/2002 |
| WO | WO 2004071406 A2 * | 8/2004 |

OTHER PUBLICATIONS

Newham, Eur. J, Appl. Physiol. (1988) 57:363-359.*
Omoigui, Law of Pain; The origin of all pain is inflammation and inflammatory response, 2002, Chapter 1.*
Masayo Kojima, Arthritis & Rheumatism (Arthritis Care & Research) vol. 61, No. 8, Aug. 15, 2009, pp. 1018-1024.*
Lucia et al Neuroscience Letters 431; Lucia et al, Neuroscience letters, 2008, 106-111.*
Nk et al, Arch Int Pharmacodyn Ther. Feb. 1978;231(2):340-50.*
Persky et al, Pharmacol Rev 53:161-176, 2001.*
Gunji et al, Rheumatol Int (2000) 19:95-100.*
WebMD, http://www.webmd.com/osteoarthritis/guide/arthritis-inflammation, accessed on Feb. 5, 2015.*
Brownlee et al, vol. 255, Issue 6596, Jan. 28, 1950, pp. 157-159.*
Lee et al, Lancet. Sep. 15, 2001; 358(9285):903-11.*
A. Dox et al., "Esterification of Creatine", J. Biol. Chem., 67: 671-673 (1922).
K. Ishihara et al., "An Extremely Simple, Convenient, and Selective Method for Acetylating Primary Alcohols in the Presence of Secondary Alcohols", J. Org. Chem., 58: 3791-3793 (1993).
T. McGuire et al., "Release of prostaglandin E-2 in bovine brain endothelial cells after exposure to three unique forms of the antifungal drug amphotericin-B: role of COX-2 in amphotericin-B induced fever", Life Sciences, 72: 2581-2590 (2003).
S. Wright et al., "Convenient Preparations of t-Butyl Esters and Ethers from t-Butanol", Tetrahedron, 38(42): (1997) 7345-7348.
G. Edgar et al., "The Equilibrium Between Creatine and Creatinine, in Aqueous Solution. The Effect of Hydrogen Ion", J. Amer. Chem. Soc., 47: 1179-1188 (1925).
N.K. Khanna et al., "Studies on the Anti-Inflammatory Activity of Creatine", Arch. int. Pharmacodyn., 231: 340-350 (1978).

(Continued)

*Primary Examiner* — Jean P Cornet
(74) *Attorney, Agent, or Firm* — Smith, Gambrell & Russell, LLP

(57) ABSTRACT

The present invention provides a creatine ester anti-inflammatory compound which may be received by animals and then metabolized into a biologically active form of creatine. The biologically active creatine inhibits the production of chemical mediators, released during an inflammatory response, which are important components in the inflammatory response and the inflammation and pain resulting from physical or chemical trauma to cells and tissue.

18 Claims, 18 Drawing Sheets

(56) References Cited

OTHER PUBLICATIONS

K. S. Mark et al., "Tumor Necrosis Factor-alpha Induces Cyclooxygenase-2 Expression and Prostaglandin Release in Brain Microvessel Endothelial Cells", J. Pharmacol. Exp. Ther., 297: 1051-1058 (2001).
K. Wakasugi et al., "Diphenylammonium triflate (DPAT): efficient catalyst for esterification of carboxylic acids and for transesterification of carboxylic esters with nearly equimolar amounts of alcohol", Tetrahedron Lett., 41: 5249-5252 (2000).
B.R. Madan et al., "Effect of Creatine on various experimentally induced inflammatory models", Indian J. Physiol. Pharmacol., 23(1): 1-7 (1979).
K.S. Mark et al., "Increased Permeability of Primary Cultured Brain Microvessel Endothelial Cell Monolayers Following TNF-alpha Exposure", Life Sciences, 64(21): 1941-1953 (1999).
Rak, J., "Thermal Properties, Crystal Lattice Energy, Mechanism and Energetics of the Thermal Decomposition of Hydrochlorides of 2-Amino Acid Esters", Thermochimica Acta, 171: 253-277 (1990).
Yadav, J.S. et al., "Zinc Promoted Mild and Efficient Method for the Esterification of Acid Chlorides with Alcohols", Synthetic Communications, 28(13): 2337-2342 (1998).
L. Weixing et al., Identification of GS 4104 as an Orally Bioavailable Prodrug of the Influenza Virus Neuraminidase Inhibitor GS 4071, Antimicrobial Agents and Chemotherapy, 42(3): 647-653 (1998).
T. Prueksaritanont et al., In vitro and in vivo evaluations of the metabolism, pharmacokinetics, and bioavailability of ester prodrug of L-767,679 a potent fibrogen receptor antagonist, Drug Metabolism and Disposition, 25(8): 978-984(1997).

\* cited by examiner

R = Et, Benzyl, and the like

X = Stearate, Palmitate, Oleate, Lauryl Sulfate, Chloride, Acetate, Succinate, Mesylate, Sulfate, Citrate, and the like R = Ethyl, Benzyl, and the like

CREATINE ESTER ANTI-INFLAMMATORY COMPOUNDS AND FORMULATIONS

CROSS REFERENCE TO RELATED APPLICATIONS

This application is a continuation of U.S. patent application Ser. No. 11/955,681, filed Dec. 13, 2007, (now abandoned), which is a continuation-in-part of U.S. patent application Ser. No. 10/365,666, filed Feb. 12, 2003 (now abandoned), which is a continuation-in-part of International Application No. PCT/US01/28788, filed in the United States of America on Sep. 14, 2001. The Patent Cooperation Treaty Application PCT/US01/28788 claimed priority under 35 U.S.C. §119(e) to U.S. Provisional Patent Application 60/232,969, filed Sep. 14, 2000. U.S. patent application Ser. Nos. 11/955,681, 10/365,666, International Application No. PCT/USO1/28788 and U.S. Provisional Patent Application 60/232,969 are herein incorporated by reference in their entirety.

This invention was made with government support under contract/grant number R43-AT01145-01 awarded by the SBA/NTH. The Government has certain rights in this invention.

FIELD OF THE INVENTION

The present invention generally relates to the field of creatine, and particularly to an anti-inflammatory creatine compound.

BACKGROUND OF THE INVENTION

The treatment of inflammation and the pain, swelling, fever, and the like, associated with inflammation using anti-inflammatory agents is commonplace. Regardless of the type of pain, whether acute as in stings, ankle sprains, broken bones, and the like, or chronic from disease states as in neurodegeneration, arthritis, septic shock, fibromyalgia, interstitial cystitis, migraine, neuropathic pain syndromes, reflex sympathetic dystrophy, vulvar vestibulitis syndrome, and the like, pain arises from inflammation and the inflammatory response. The inflammatory response is a process involving the release of various chemical mediators.

The inflammatory response is a cellular cascade of these chemical mediators operating in a complimentary and synergistic fashion. One class of potent inflammatory mediators is the arachidonic acid metabolites that include various thromboxanes, leukotrienes and prostaglandins. Thromboxanes, leukotrienes and prostaglandins are released from cells in response to injury and infection, activate local nerve receptors and nerve terminals, and are associated with increases in vascular permeability (edema), blood cell adhesion, and temperature.

A simplification of a process through which a prostaglandin is created is as follows: Injury occurs to tissue and the cells within; Blood cells (basophils, mast cells and platelets) release inflammatory mediators (e.g., serotonin, histamine); subsequent to the binding of these mediators with nerve receptors, the adjacent nerves and nerve endings (i.e., C-fibers and A-delta fibers which carry pain impulses to the brain) release inflammatory peptide proteins (e.g., Substance P, Calcitonin, Calcitonin Gene Related Peptide), concomitantly clotting factors in the blood produce and activate inflammatory mediator peptide proteins (e.g., Neurokinin A, Bradykinin, Kallidin and T-kinin); these peptide proteins activate phospholipids embedded in the cell membrane causing the release of Lipid Peroxides (i.e., Archidonic Acid); cyclooxygenase, a cell membrane bound enzyme produced during cell inflammation, oxidizes the lipid peroxide to synthesize prostaglandin.

Many of the currently available analgesic agents (i.e., corticosteroid anti-inflammatories and non-steroidal anti-inflammatories) function by inhibiting the production of the arachidonic acid metabolites, either selectively, through inhibiting cyclooxygenase 2, or non-selectively through inhibition of both cyclooxygenase I and 2. Unfortunately, many anti-inflammatory products have acute and chronic safety issues that limit their application. For example, the non-steroidals inhibitory activity with regard to cyclooxygenase may create problems associated with gastric and renal toxicity, such as ulcers and serious complications such as bleeding, perforations, and obstructions. Further, a user of non-steroidal anti-inflammatory agents may be required to co-administer a gastric protectant when administering the anti-inflammation agent in order to avoid the harmful effects.

Creatine has been studied as an alternative to the use of corticosteroids and non-steroidal anti-inflammatory agents. Creatine has been shown to possess anti-inflammatory activity. See Khanna, N K and Madan, B R. *Studies on the anti-inflammatory activity of creatine*. Arch Int Pharmacodyn Ther 231(2): 340-350, February 1978, which is herein incorporated by reference in its entirety. This activity has been shown orally effective in suppressing the inflammatory responses produced by carrageenan, 5-hydroxytryptamine, nystatin and formaldehyde. See Madan, B R. and Khanna N K. *Effect of creatinine on various experimentally induced inflammatory models*. Indian J. Physiol Pharmacol 23(1): 1-7, January-March 1979, which is herein incorporated by reference in its entirety. Subsequent studies have further confirmed the anti-inflammatory activity of creatine alone and in combination with other anti-inflammatories, See Khanna, N K. and Tahashildar, J. *Anti-inflammatory activity of Creatine and Indomethacin Drug Mixture in Rats*. Indian Journal of Experimental Biology 23: 402-403, July 1985, which is herein incorporated by reference in its entirety. Unfortunately, the use of creatine as an anti-inflammatory has been limited due to high dosage requirements, limited bio-availability characteristics, and as yet unknown interaction characteristics within the inflammatory response.

Consequently, it would be desirable to provide an anti-inflammatory compound which altered the inflammatory cascade at a point prior to cyclooxygenase activation of the arachidonic acid metabolites. Such a compound may avoid the harmful side effects, such as gastric and renal toxicity, associated with currently used anti-inflammatory agents. Further, it would be desirable to provide a method of delivering an anti-inflammatory compound, which enabled effective amounts of the active anti-inflammatory agent within the compound to reach the cell undergoing an inflammatory cascade and be modified into the active agent by the host system. Additionally, it would be desirable to provide a method of inhibiting prostaglandin synthesis, an arachidonic acid metabolite, during a cellular inflammatory cascade.

Still further, it would be desirable to provide an anti-inflammatory compound in tolerable dosages capable of altering the cellular inflammatory cascade and providing relief from associated inflammation, pain, swelling, fever, and the like. Finally, it would be desirable to provide pain relief through use of an anti-inflammatory creatine compound which is safer, more tolerable, and has increased bio-availability, for inhibiting inflammation and the inflammatory response.

SUMMARY OF THE INVENTION

Accordingly, the present invention is directed to creatine ester anti-inflammatory compounds. In a first aspect of the present invention, a method for inhibiting inflammatory response in an animal includes receiving a creatine ester by the animal. The creatine ester is suitable to be modified by the animal to form creatine. The increased absorption and delivery of creatine into a target cell results in more cellular creatine available for inhibiting the production and/or release of inflammatory mediators from the cell.

In a second aspect of the present invention, a method for inhibiting prostaglandin synthesis in an animal includes receiving a creatine ester by the animal. The creatine ester is suitable for being modified by the animal to form creatine. The increased absorption and delivery of creatine into a target cell results in more cellular creatine available for inhibiting the production and/or release of inflammatory mediators, such as prostaglandin, by altering the cellular inflammatory cascade at a point prior to the activation of arachidonic acid by the cyclooxygenase.

In a third aspect of the present invention, an anti-inflammatory creatine compound includes a creatine ester. The creatine ester is suitable for being modified to form creatine, which acts as the anti-inflammatory.

In a fourth aspect of the present invention, a method for providing pain relief includes receiving a creatine ester by an animal. Wherein the creatine ester is suitable for being modified by the animal to form creatine.

It is an object of the present invention to provide an anti-inflammatory compound which is effective in inhibiting the inflammatory response and may be administered in tolerable dosage amounts. By altering the inflammatory cascade at a point prior to cyclooxygenase activation of arachidonic acid metabolites the anti-inflammatory compound of the present invention avoids the harmful side effects, such as gastric and renal toxicity, associated with many currently available anti-inflammatories.

It is a further object of the present invention to provide a method of delivering an anti-inflammatory compound which improves the bioavailability characteristics of the anti-inflammatory agent. The result being that a higher concentration of the active ingredient of the anti-inflammatory compound of the present invention reaches the site of inflammation.

Additionally, an object of the present invention is to provide a method for inhibiting the production and/or release of arachidonic acid metabolites. Prostaglandins are known, potent chemical mediators of the cellular inflammatory cascade, thus by inhibiting their production the anti-inflammatory compound of the present invention may lessen the severity of an inflammatory cascade.

It is a still further object of the present invention to provide relief from the pain, swelling, fever, and the like, associated with inflammation caused by an inflammatory response. The inflammatory response, being initiated by the physical or chemical injury to a cell or tissue, causes an inflammatory cascade of chemical mediators. The anti-inflammatory compound of the present invention alters this inflammatory cascade and effectively blocks production of the chemical mediators. This results in a decreased inflammatory response and concomitant decrease in inflammation, pain, swelling, fever, and the like, associated with it.

It is to be understood that both the forgoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

Figure 1A:
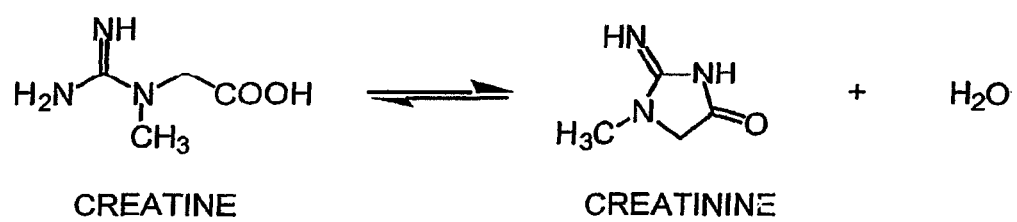
FIG. 1A is an illustration depicting conversion of creatine to creatinine.
Figure 1B:
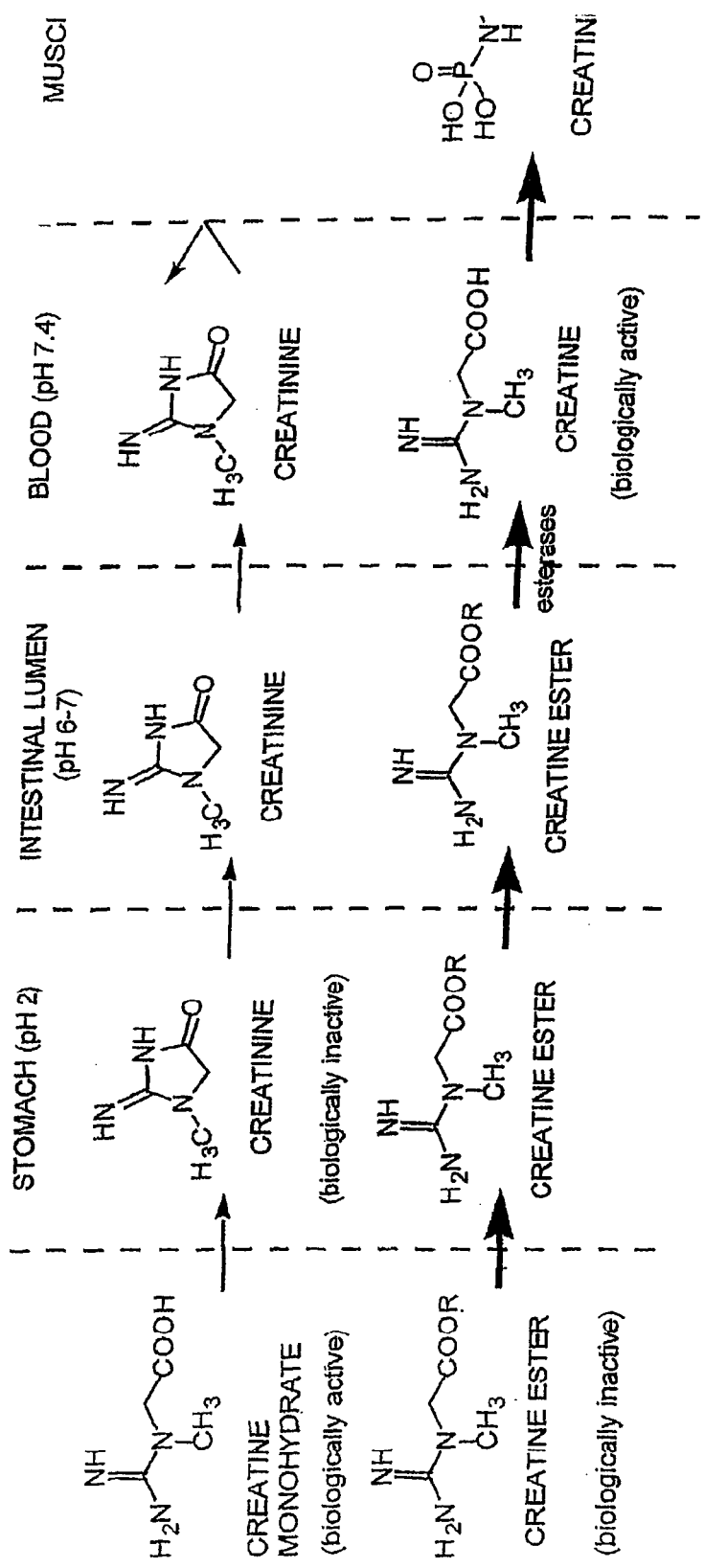
Figure 1C:
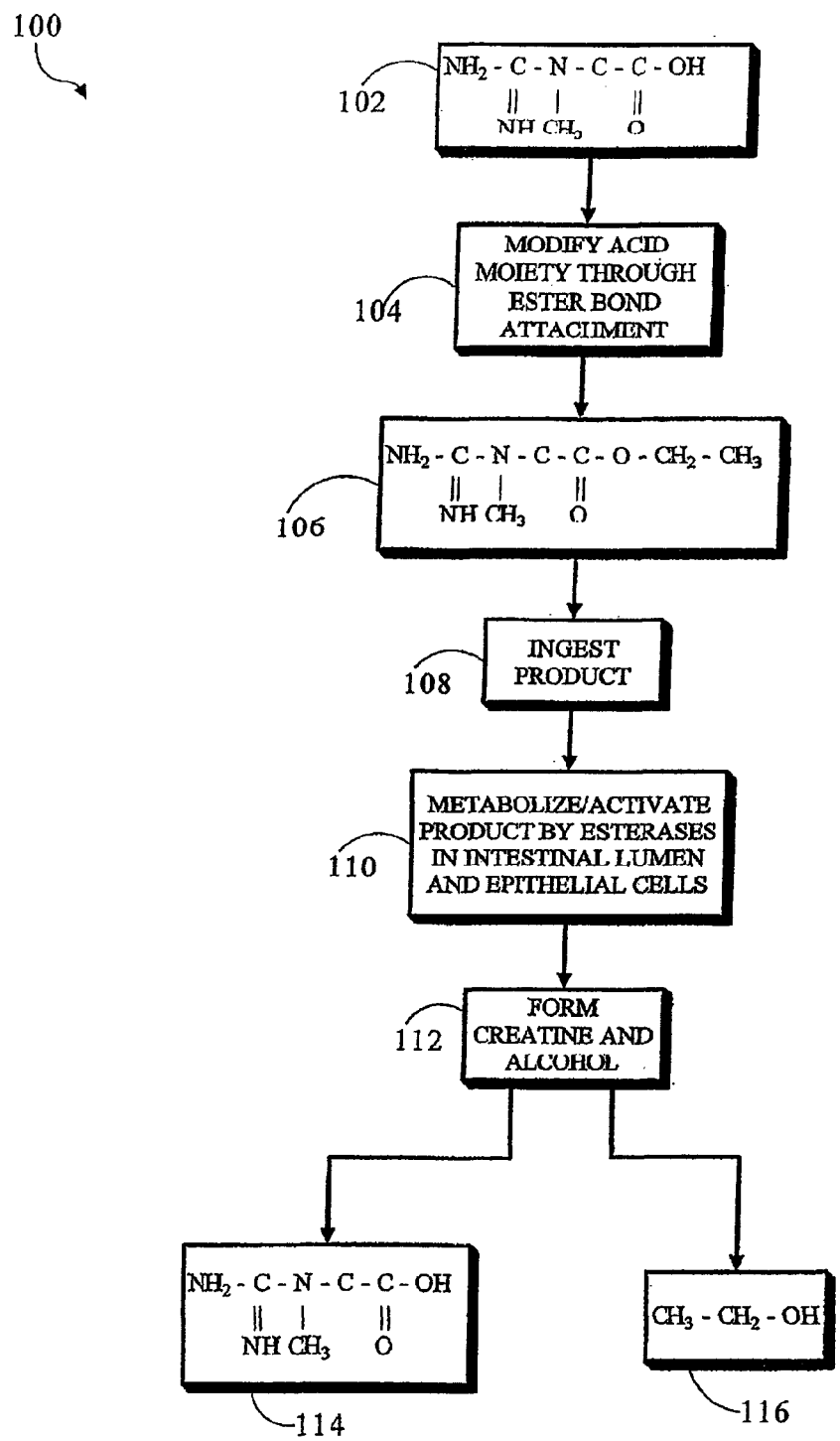
Figure 1D:
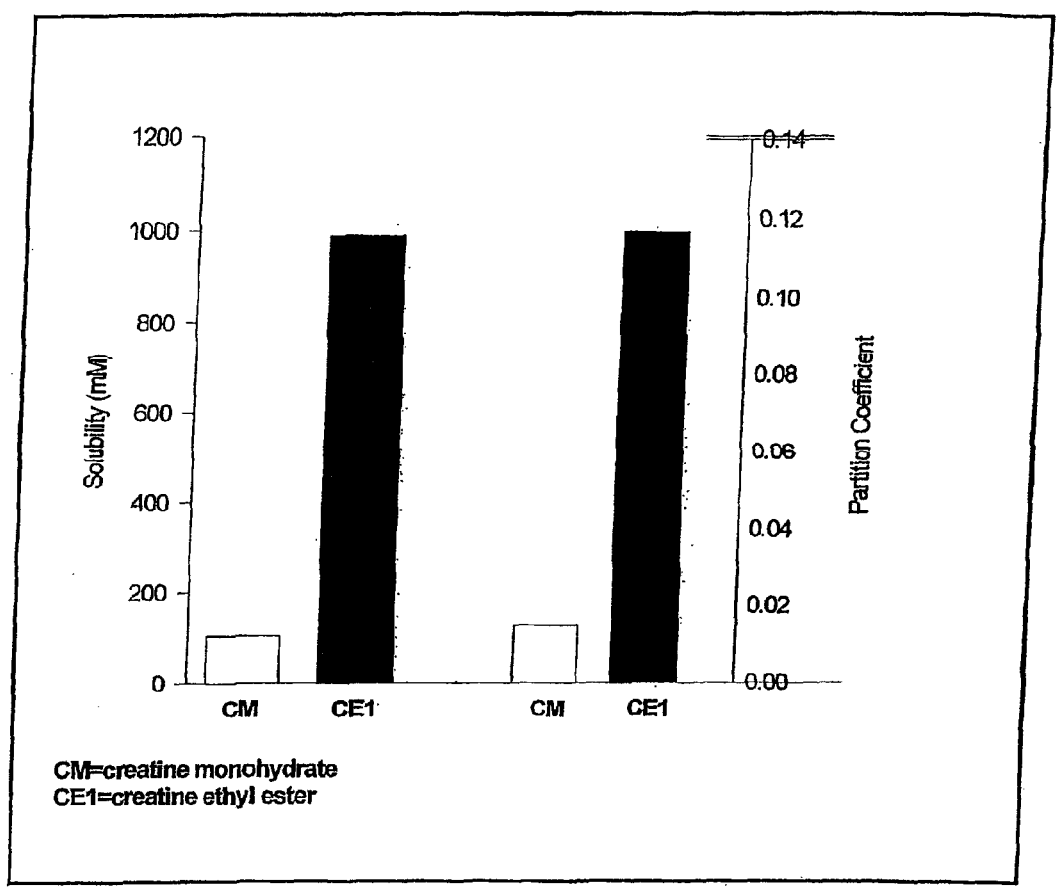
Figure 2A:
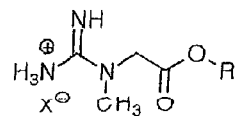
Figure 2B:
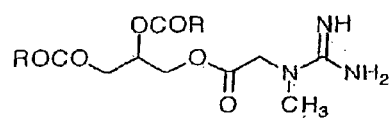
Figure 2C:
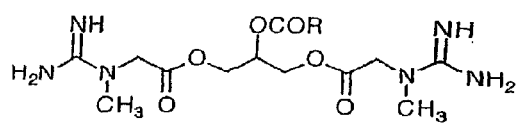
Figure 2D:
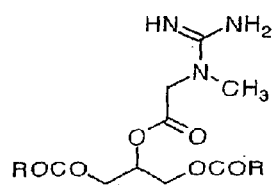
Figure 2E:
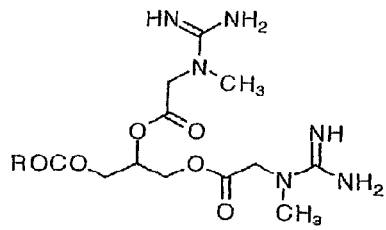
Figure 2F:
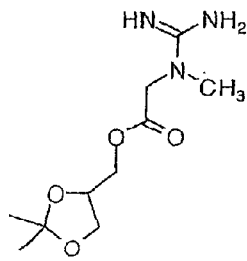
Figure 2G:
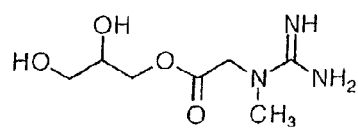
Figure 2H:
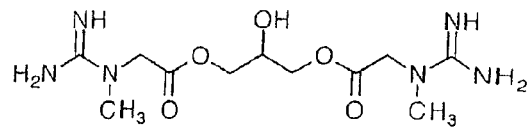
Figure 2I:
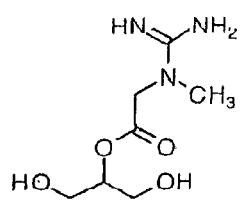
Figure 2J:
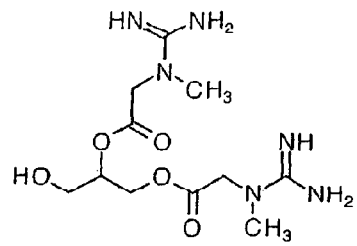
Figure 2K:
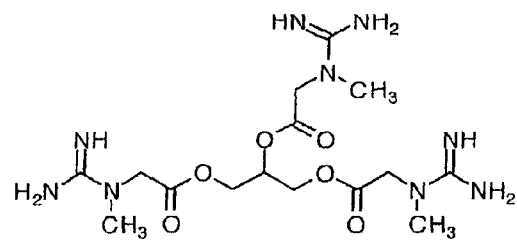
Figure 2L:
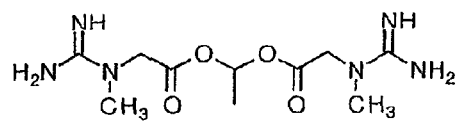
Figure 2M:
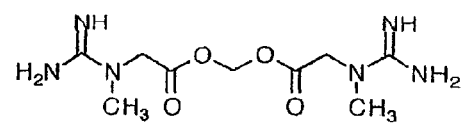
Figure 2N:
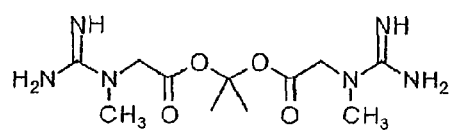
Figure 3:
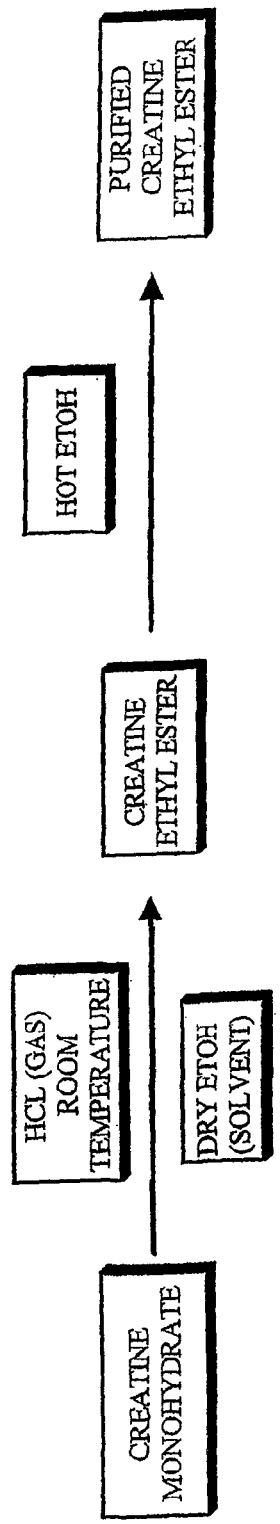
Figure 4:
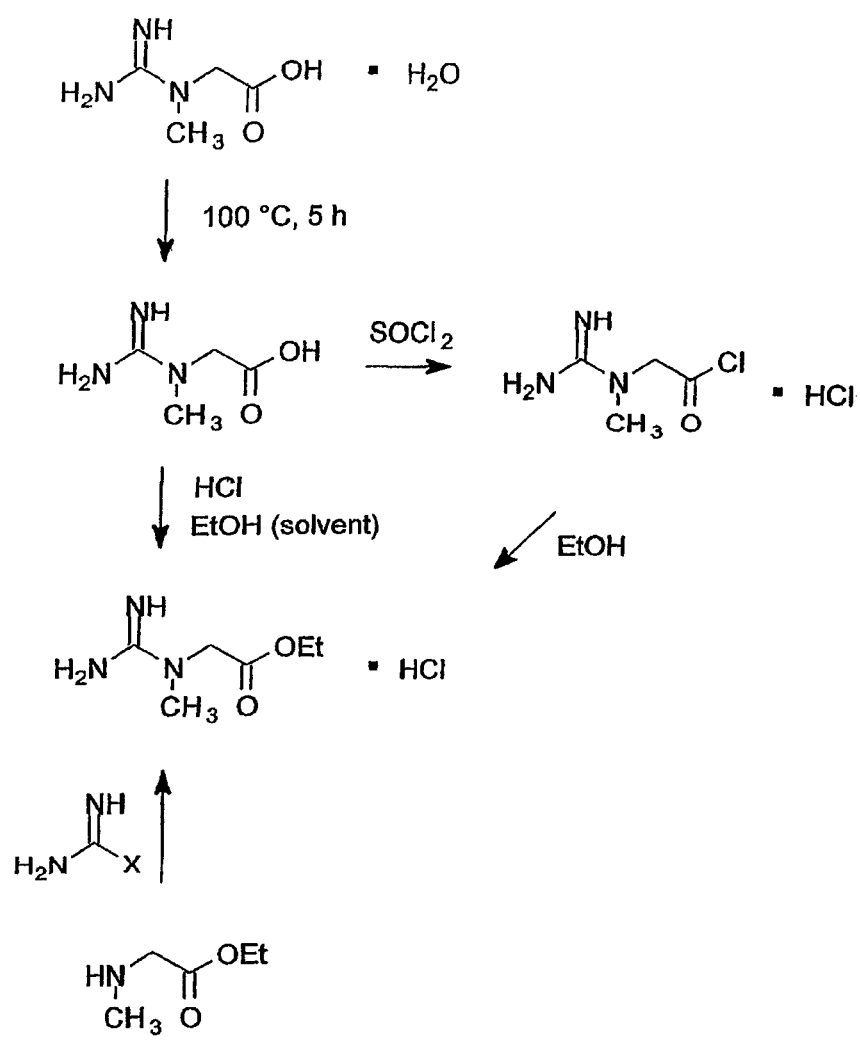
Figure 5:
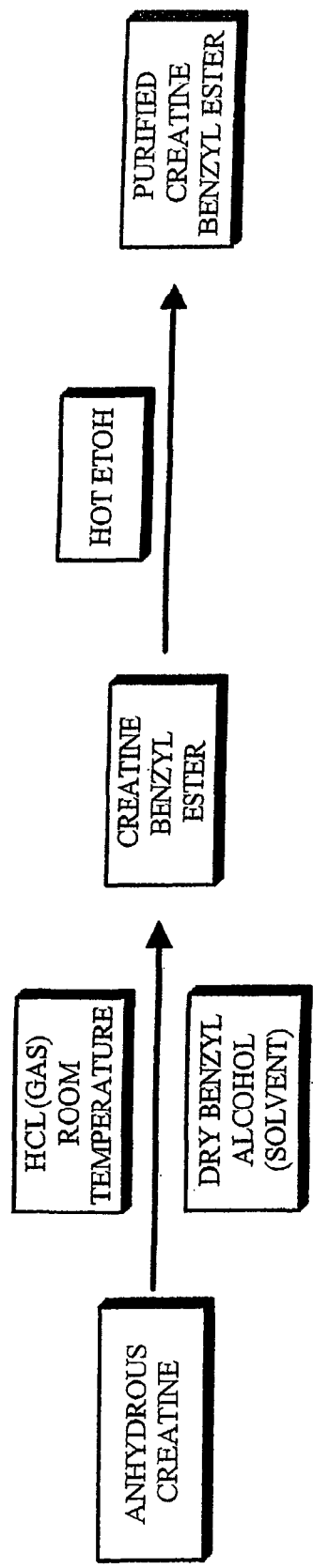
Figure 6:
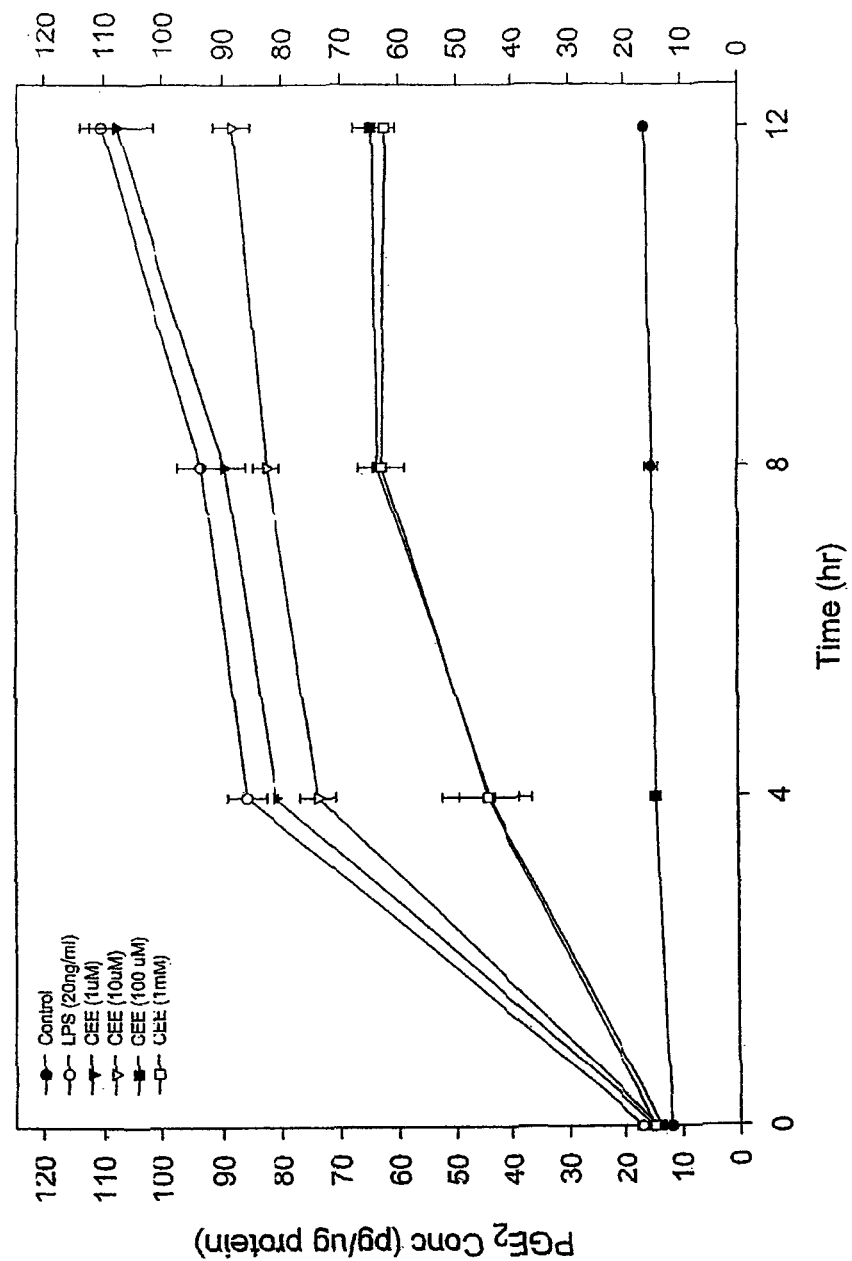
Figure 7:
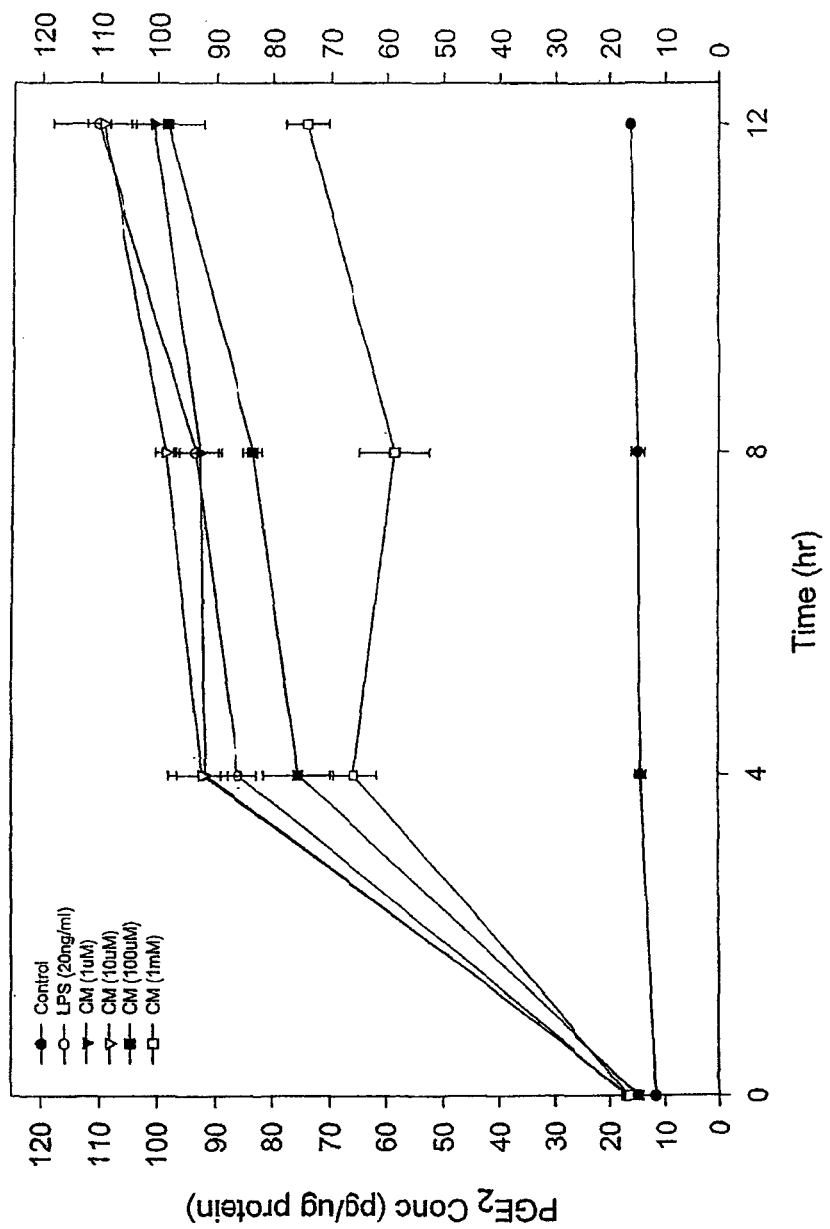
Figure 8:
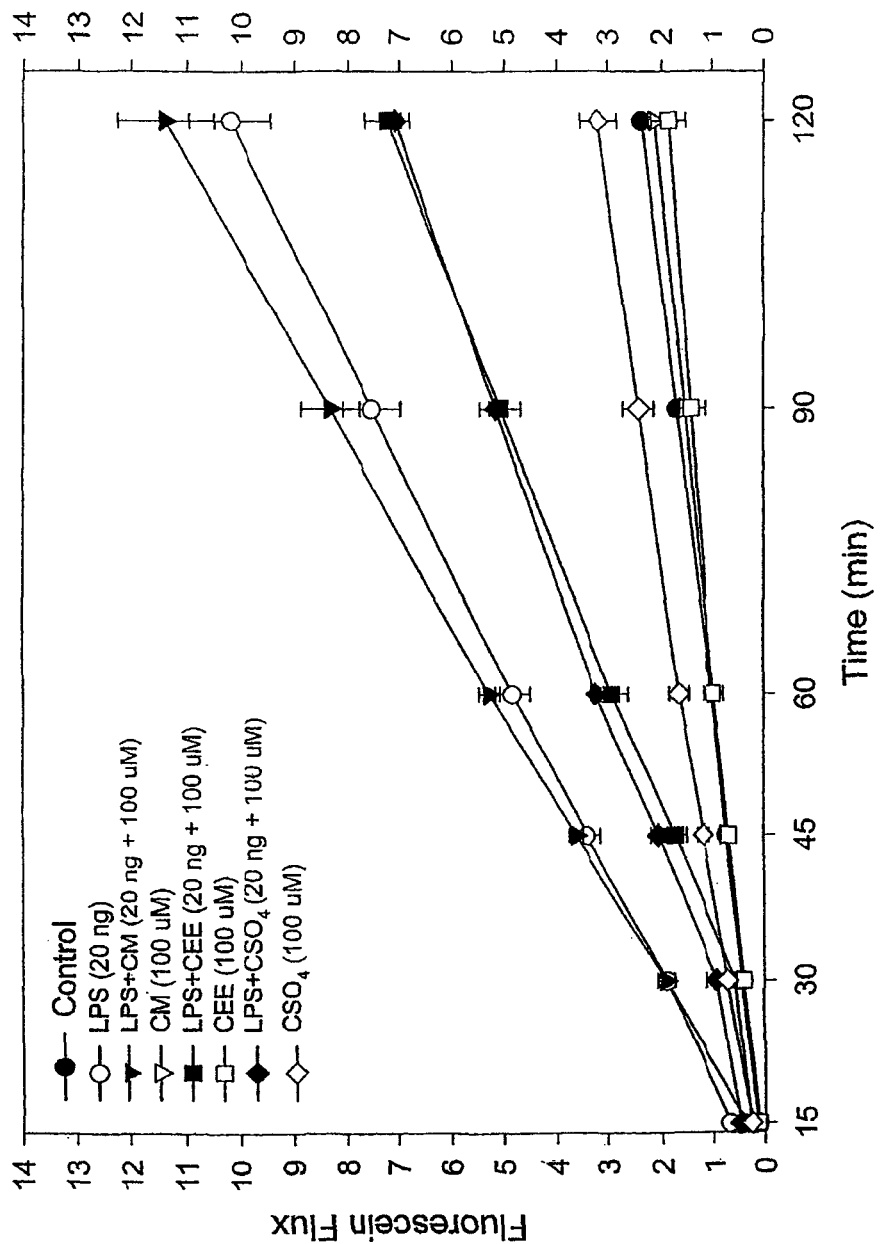
Figure 9:
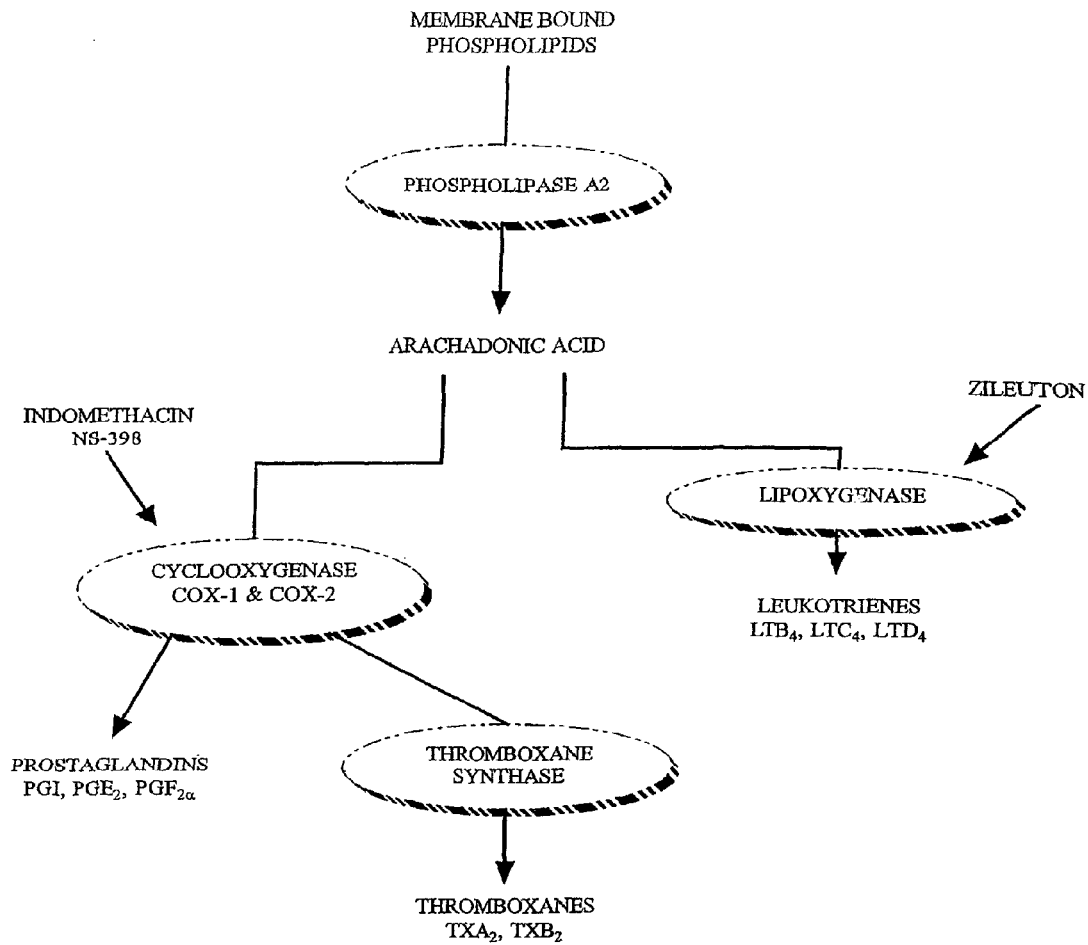
Figure 10:
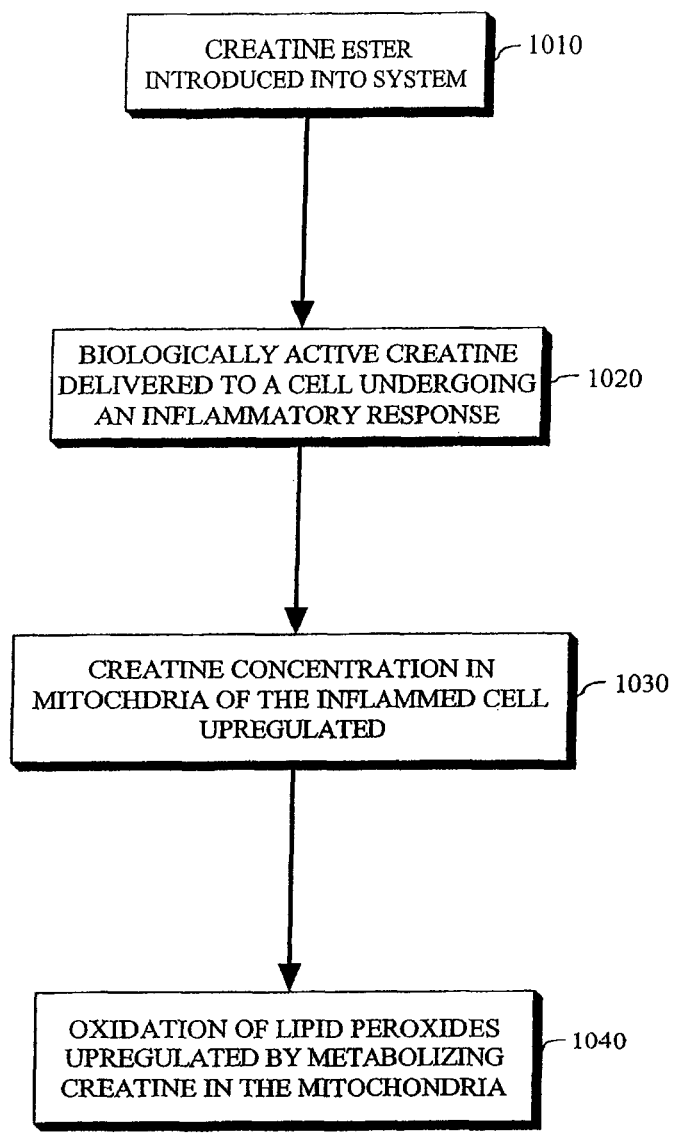
Figure 11:
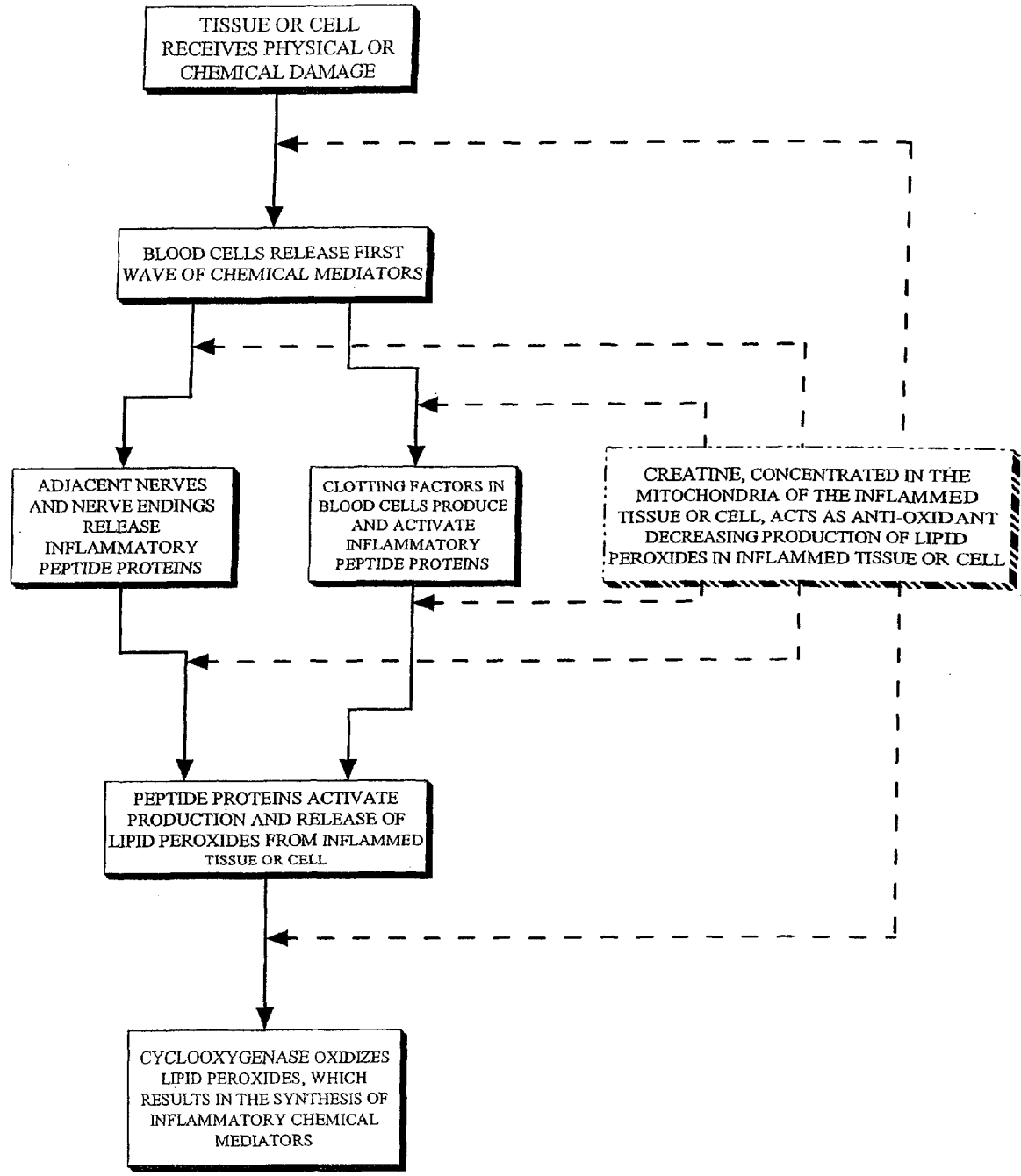
Figure 12:
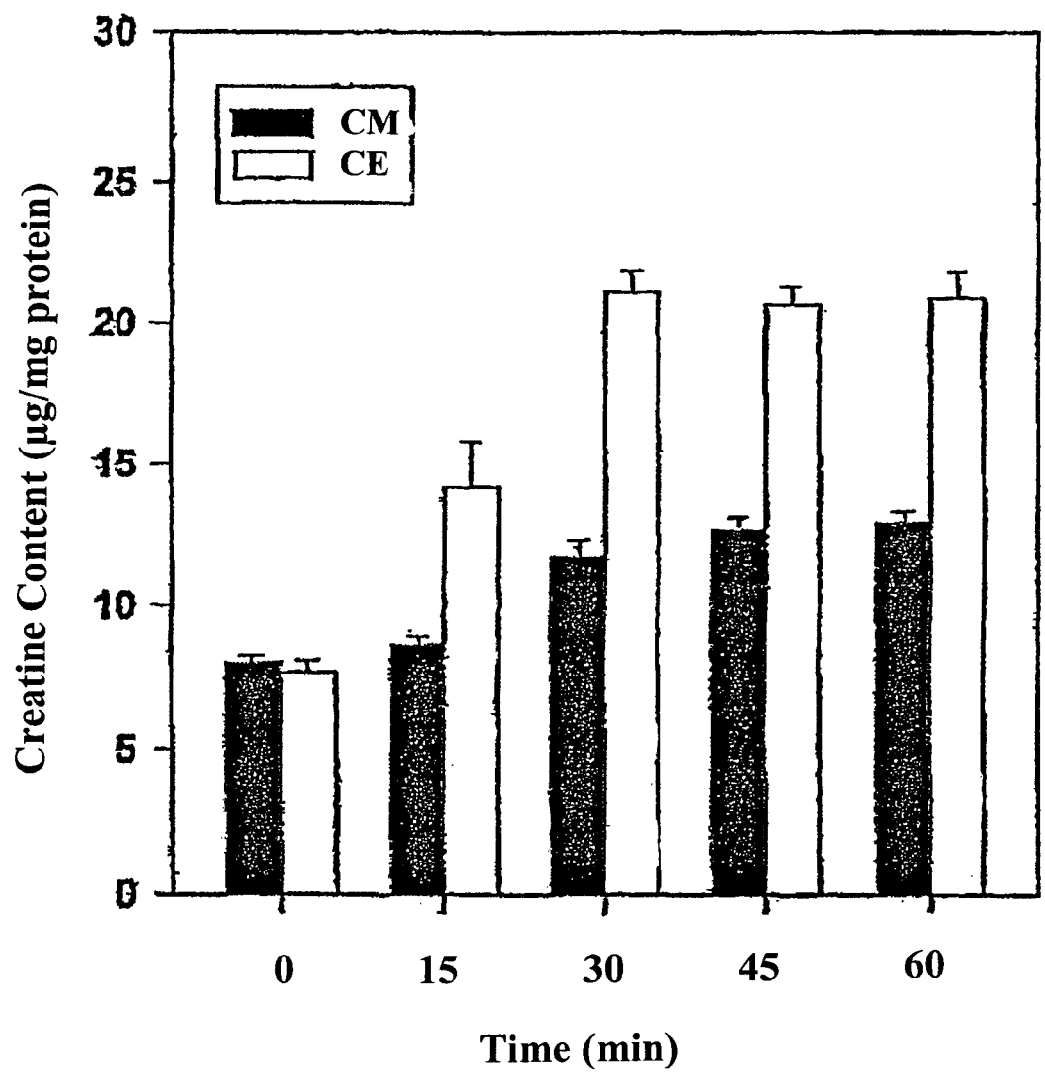
Figure 13:
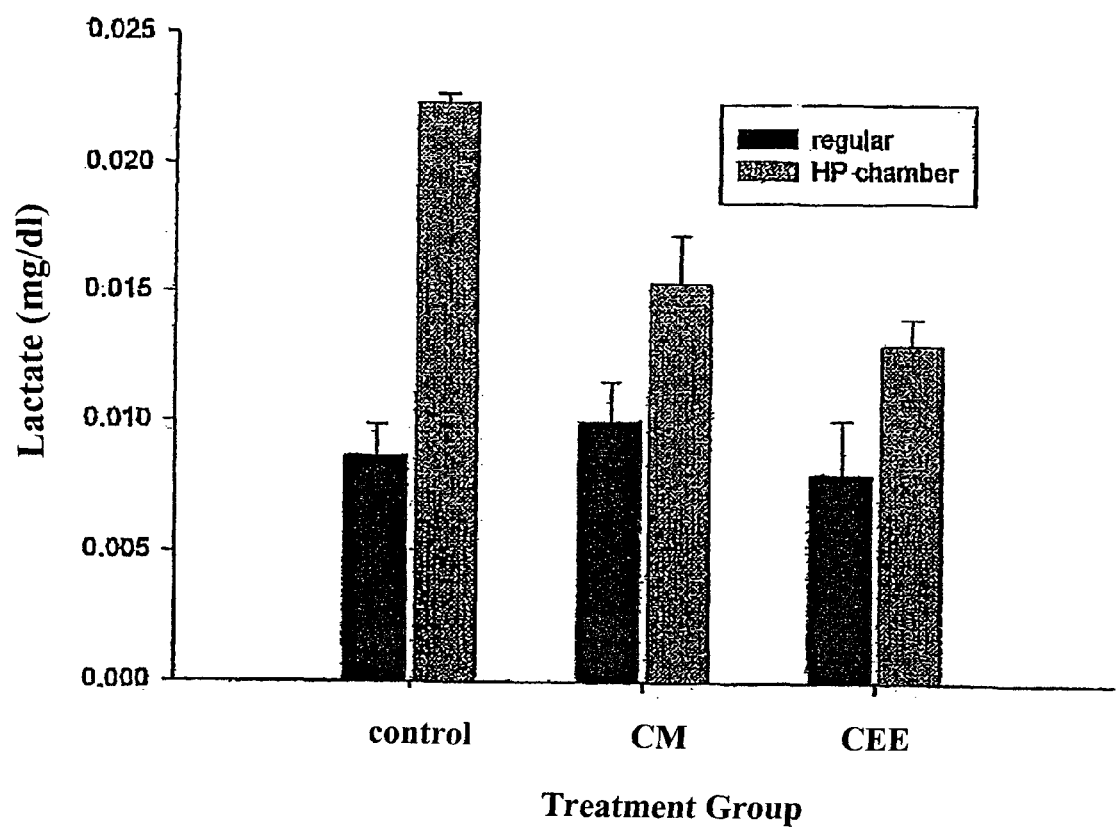
Figure 15:
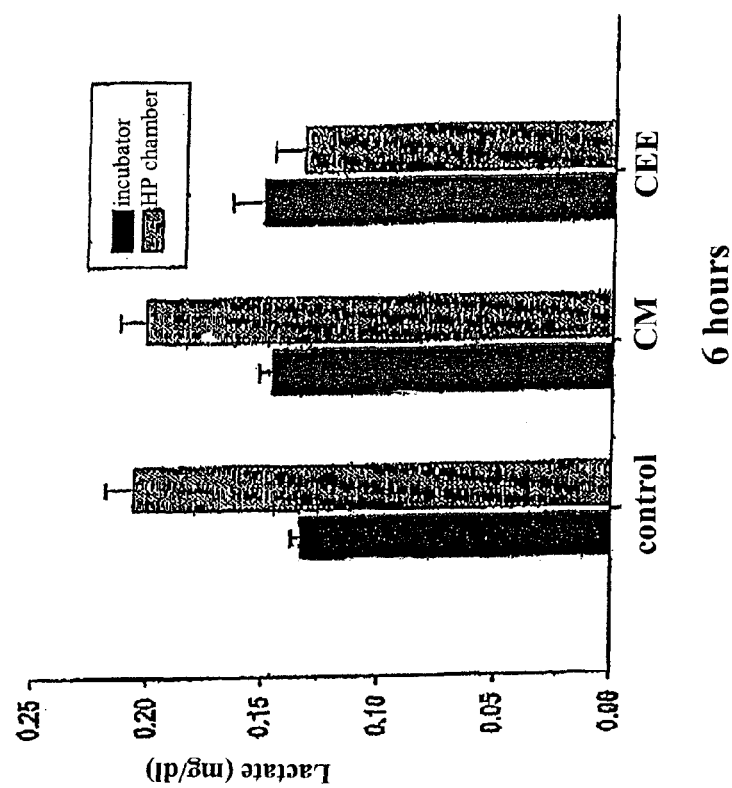
Figure 14:
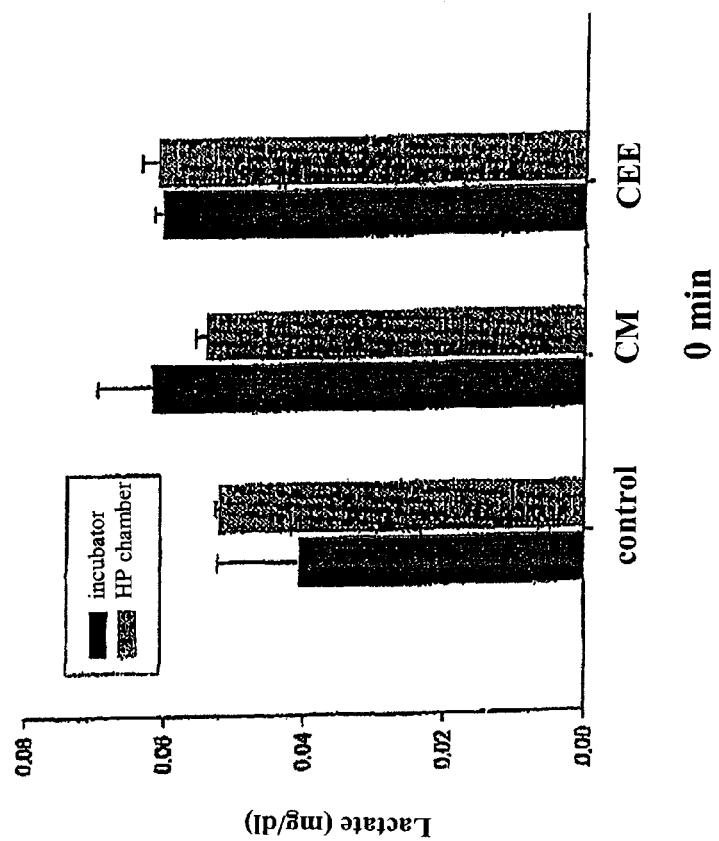

FIG. IB is a depiction of an exemplary embodiment of the present invention wherein the processing of creatine monohydrate versus a creatine ester by the body is shown;

FIG. 1C is a flow diagram illustrating an exemplary embodiment of the present invention wherein a pronutrient derivative of creatine is created through the modification of an acid moiety by ester bond attachment;

FIG. ID is an illustration of an embodiment of the present invention in which a graph depicting solubility and partition coefficients of creatine ethyl ester versus creatine monohydrate are shown;

FIGS. 2A, 2B, 2C, 2D, 2E, 2F, 2G, 2H, 2I, 2J, 2K, 2L, 2M and 2N are of exemplary compounds of the present invention;

FIG. 3 is an illustration depicting an exemplary embodiment of the present invention wherein a creatine ethyl ester compound is produced by solvating creatine monohydrate in dry ethyl alcohol in an acidic atmosphere;

FIG. 4 is an illustration of an embodiment of the present invention wherein additional methods and processes are shown for the production of a creatine ester;

FIG. 5 is an illustration depicting an exemplary embodiment of the present invention wherein a creatine benzyl ester compound is produced by solvating anhydrous creatine in dry benzyl alcohol in an acidic atmosphere;

FIG. 6 is a graphical representation of the amount of prostaglandin E2 released from confluent mono layers of brain microvessel endothelial cells exposed to bacterial lipopolysaccharide (20 ng/ml) either alone, or in the presence of various concentrations of creatine ethyl ester hydrochloride salt;

FIG. 7 is a graphical representation of the amount of prostaglandin E2 released from confluent monolayers of brain microvessel endothelial cells exposed to bacterial lipopolysaccharide (20 ng/ml) either alone, or in the presence of various concentrations of creatine monohydrate;

FIG. 8 is a graphical representation of the anti-inflammatory effects of creatine ethyl ester on lipopolysacharride-induced increases in brain microvessel endothelial cells monolayer permeability;

FIG. 9 is a schematic illustration of the arachidonic acid metabolite cascade, which results in the formation of inflammatory mediators;

FIG. 10 is an illustration of an exemplary embodiment of the present invention wherein a creatine ethyl ester compound acts as an anti-oxidant when received in the mitochondria of a cell;

FIG. 11 is an illustration depicting stages of a cellular inflammatory response process and an anti-inflammatory interruption of the process by the creatine ethyl ester compound of the present invention;

FIG. 12 is a graphical representation of the improved bio-availability of the creatine ethyl ester compound of the present invention in C2C12 muscle cells versus creatine monohydrate;

FIG. 13 is a graphical representation of cellular lactic acid levels in a treatment group of C2C12 muscle cells comprising control cells, creatine monohydrate exposed cells, and creatine ethyl ester exposed cells, under normal and hypoxic conditions;

FIG. 14 is a graphical representation of lactic acid release from the treatment group of C2C12 muscle cells under normal and hypoxic conditions at zero minutes; and FIG. 15 is a graphical representation of lactic acid release from the treatment group of C2C12 muscle cells under normal and hypoxic conditions at six hours after exposure.

DETAILED DESCRIPTION OF THE INVENTION

Reference will now be made in detail to the presently preferred embodiments of the invention, examples of which are illustrated in the accompanying drawings. Creatine itself presents anti-inflammatory characteristics. These may include an alteration of the cellular inflammatory cascade at a point prior to cyclooxygenase activation of arachidonic acid metabolites resulting in the synthesis of prostaglandin. However, creatine itself is poorly soluble in an aqueous solution. Further, creatine is not well absorbed from the gastrointestinal (GI) tract, having a total estimated oral absorption of fourteen percent (14%) or less of the administered dose. Thus, current products require large amounts of creatine to be administered to be effective, typically 5 grams or more. Additionally, side effects such as bloating, gastrointestinal (GI) distress, diarrhea, and the like are encountered with these high dosages.

Creatine, N-aminoiminomethyl-N-methylglycine, is an endogenous nutrient which may be produced in the liver and kidneys. Typically, creatine is produced by the transfer of the guanidine moiety of arginine to glycine, which is then methylated to give creatine. Creatine may be represented by the following formula:

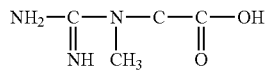

Studies in the laboratory have shown that the aqueous solubility and partition coefficient of creatine monohydrate, shown above, are 15.6±2.1 mg/mL and 0.015±0.007, respectively. The low oral bioavailability of creatine may derive not only from its low lipophilicity and concomitant poor membrane permeability, but also from rapid conversion to creatinine in the acidic condition of the stomach, and shown in FIG. 1A.

At a gastric pH range of 1-2, the equilibrium between creatine and creatinine shifts to the right such that the creatinine/creatine ratio may be greater than or equal to 30. See Edgar, G.; Shiver, H. E., *The Equilibrium Between Creatine and Creatinine in Aqueous Solution. The Effect of Hydrogen Ion.* J. Amer. Chem. Soc. 1925, 47, 1179-1188, which is herein incorporated by reference in its entirety.

Referring generally now to FIGS. 1B through 5, exemplary embodiments of the present invention are shown.

in a preferred embodiment of the present invention, FIG. 1B shows creatine ester metabolism, wherein the creatine is combined with an ester to form a compound with increased bioavailability characteristics. Oral bioavailability is dependent on both the permeability and solubility of the compound. Permeability is the ability of a compound to penetrate across a barrier, such as a membrane, cell wall, and the like, wherein solubility refers to the amount of the compound that may be dissolved within an aqueous solution. The bioavailability of a compound may determine its efficacy once introduced into a system, such as a digestive system, vascular system, and the like. By providing a creatine ester, a more water-soluble compound will be provided than the relatively insoluble zwitterionic creatine, and increased lipophilicities will allow for better membrane permeability.

Standard creatine containing supplements, such as creatine monohydrate, undergo substantial conversion to creatinine in the stomach. As a result, creatine intestinal absorption is low which leads to reduced amounts of creatine absorbed into the blood and ultimately less creatine reaching the target cell. By masking the carboxylic acid functional group of creatine through esterification, the formation of creatinine in the stomach will be prevented, resulting in an efficient delivery of the creatine esters to the intestine where absorption into the bloodstream may occur.

The increased stability and improved absorption of creatine ester results in much greater blood creatine levels than may be achieved with other standard creatine supplements. As a result, the increased blood levels of creatine obtained with the creatine ester anti-inflammatory compounds are expected to result in increased creatine concentrations at the target tissue (i.e. tissue undergoing an inflammatory response or inflamed tissue).

As the creatine ester compound moves from the intestinal tissue into the bloodstream, and finally the target tissue, the creatine ester compounds themselves are biologically inactive. The creatine ester compounds are converted to the biologically active form of creatine by esterase enzymes present in both the cells and the bloodstream. Thus, the advantages of the creatine ester (i.e., increased solubility and permeability) are preserved during absorption and tissue distribution, but once in the blood and/or target cells the creatine ester is converted back into its biologically active form to aid in reducing the production of inflammation mediators.

Referring now to FIG. IC, an exemplary embodiment of the present invention is shown wherein an anti-inflammatory derivative of creatine is created through the modification of an acid moiety by ester bond attachment. Creatine is changed by modifying an acid moiety through ester bond attachment. For example, creatine may be converted to creatine ethyl ester, which has a formula as follows:

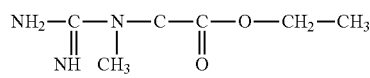

A creatine ester has the advantages of increased aqueous solubility and increased absorption from the gastrointestinal (GI) tract resulting in increased bioavailability. Increased bioavailability results in fewer gastrointestinal side effects. Further, more varied formulation possibilities are feasible, for example, the product may be formulated in tablet or capsule form with dextrose and/or phosphate for ease of use and effectiveness. The creatine ester compound may alternatively be formulated as a suspension, emulsion, or sterile solution, which allows for parenteral and/or topical delivery, via injection and topical delivery, via direct application to the inflamed tissue, and the like as discussed below in FIG. 10.

As mentioned above, administration of the product may occur through ingestion, parenteral methods (i.e., injection, suppository), topical application, and the like. Once administered, the body metabolizes and activates the creatine ester by esterases, found throughout the body in a variety of cells and biological fluids. The esterases convert the product to creatine and an alcohol. Thus, the current invention supplements the amount of creatine normally available thereby increasing creatine levels available for response to inflammation and the inflammatory response. This increased level of creatine availability may inhibit the inflammatory response, for example by reducing the amount of prostaglandins in the cell. Further, the resultant alcohols, such as ethanol, glycerol, benzyl alcohol, tert-butyl alcohol, are relatively harmless. See Budavari, S. (Ed.) The Merck Index. Merck and Co., Inc., Whitehouse Station, N.J., 1996, which is herein incorporated by reference in its entirety. For example, benzyl alcohol is used as a pharmaceutical preservative.

Solubility and permeability, two important factors that influence the amount of a compound available to an organism, are enhanced by the creatine ethyl ester. In terms of solubility, creatine ethyl ester is a great deal more soluble than other standard creatine compounds. Utilizing a physiological buffer solution (PBS), laboratory analysis indicates that creatine monohydrate has a solubility limit of approximately 10 mg/ml. This value may be overly generous, as a great deal of vortexing of the sample and brief heating of the sample to 37 degrees Celsius had to be performed to even achieve that result. However, the creatine ethyl ester is readily soluble in room temperature PBS with solubility over 200 mg/ml.

With regard to permeability, a laboratory analysis was performed comparing the creatine monohydrate to creatine ethyl ester in MDCK monolayers. The MDCK are a canine kidney epithelial cell line that has been used as an in vitro model for assessing drug permeability. In the MOCK mono layers, creatine monohydrate showed approximately 10% flux over one hour. In other words, 10% of the original amount of creatine monohydrate added to one side of the MDCK monolayer made it across to the other side in a 60-minute period. For creatine ethyl ester, the permeability is quite higher, averaging approximately 20% flux over one hour. Similar results are expected in a Caco-2 monolayer, which may be used as an in vitro model for intestinal absorption. Thus, the creatine ester of the present invention has the unexpected result of both increased solubility and membrane permeability, and thus greater bioavailability, as shown through the following table and graph depicted in FIG. ID, and the graph depicted in FIG. 12.

| Substance | Conc. at Saturation | Partition |
|---|---|---|
| Creatine | 15.6 +/− 2.1 | 0.015 +/− 0.007 |
| Creatine Ethyl Ester | 205.9 +/− 1.5 | 0.074 +/− 0.008 |
| Creatine Benzyl Ester | 89.26 +/− 0.8 | 0.106 +/− 0.01 |

Although a creatine ethyl ester compound has been described, it is understood that a wide variety of creatine ester compounds and salts thereof are contemplated by the present invention without departing from the spirit and scope thereof, examples of which are shown in FIGS. 2A, 2B, 2C, 2D, 2E, 2F, 2G, 2H, 2I, 2J, 2K, 2L, 2M and 2N. For mono-creatine glycerol, di-creatine glycerol, tricreatine glycerol and the like, may be utilized for the present invention, the formula for a tricreatine glycerol is as follows:

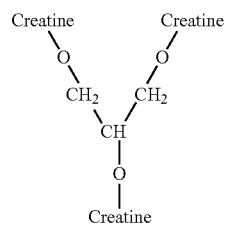

Another example of a creatine ester compound suitable for use includes creatine phosphoester, the formula of which is as follows:

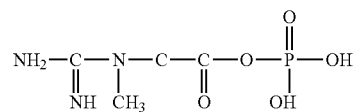

Thus, the present invention provides multiple ester derivatives of creatine, having increased solubility and permeability over creatine itself. The advantages of creatine ester compounds for anti-inflammatory response may be of further use in athletic performance markets, for example treating patients with bursitis, tendonitis, rotator cuff tears, and the like. Further, the creatine ester compounds may be useful in therapeutic markets, for example targeting patients with inflammatory pain syndromes, such as arthritis, fibromyalgia, interstitial cystitis, migraine, neuropathic pain syndromes, reflex sympathetic dystrophy, vulvar vestibulitis syndrome, and the like. Other secondary benefits may include providing treatment for hemorrhoids and reduced muscle performance/loss of muscle mass as shown and described below in FIGS. 13, 14, and 15. Additional uses pertaining to the treatment of inflammatory conditions in the livestock/animal food products market and companion animal markets are also within the scope and spirit of the present invention.

Referring generally now to FIGS. 3 and 4, an exemplary embodiment of the present invention is shown wherein the production of an ester derivative of creatine is shown. A creatine ester may be formed by reacting a hydrated form of creatine or anhydrous creatine with various alcohols in an acidic atmosphere. Under these conditions, various ester procreatine compounds may be formed, generally as white precipitates. The resultant creatine esters may be further purified by solvating in an alcohol at elevated temperatures and then cooling to form the ester procreatine compound. The final recrystallization step may not be required, as the initial precipitate is generally pure. However, such an extra step may be useful to ensure that the purest form of the creatine pronutrient has been obtained.

For example, as shown in FIG. 3, creatine monohydrate may be solvated in dry ethyl alcohol in an atmosphere of hydrochloric acid at ambient temperatures. The resultant creatine ethyl ester compound is solid at ambient temperatures. While not functionally necessary, the resultant creatine ethyl ester may be further purified with the use of ethyl alcohol at an elevated temperature to solvate the creatine ethyl ester away from possible contaminates contained in the solid reaction material. Purified creatine ethyl ester may then be achieved upon cooling the solvated creatine ethyl ester. It is understood that anhydrous creatine may also be utilized without departing from the spirit and scope of the present invention.

Although the formulation of creatine ethyl ester (CEE) is disclosed, it is understood that a variety of creatine esters may be produced utilizing analogous reaction systems without departing from the spirit and scope of the present invention. See Dox., A. W.; Yoder, L. *Esterification of Creatine*. J. Biol. Chem. 1922, 67, 671-673, which is herein incorporated by reference in its entirety. For instance, a variety of methods of producing a creatine ester are contemplated without departing from the spirit and scope of the present invention, such as the methods and process shown in FIG. 4, wherein X may include a leaving group. Although the use of creatine monohydrate (CM) is disclosed, a variety of creatine containing starting compounds is contemplated by the present invention, creatine monohydrate being disclosed merely because of its availability.

Referring now to FIG. 5, an embodiment of the present invention is shown wherein anhydrous creatine is solvated in dry benzyl alcohol in an atmosphere of hydrochloric acid at ambient temperatures to produce a creatine ester. The resultant creatine benzyl ester compound is a white solid at ambient temperatures. While not functionally necessary, the resultant creatine benzyl ester may be further purified with the use of ethyl alcohol at an elevated temperature to solvate the creatine benzyl ester away from possible contaminates. Purified creatine benzyl ester may then be achieved upon cooling the solvated creatine benzyl ester. As stated earlier, the final recrystallization step may not be required as the initial precipitate is relatively pure. However, such an extra purification step may be useful to ensure that the most pure form of the compound has been obtained.

As discussed earlier, creatine esters may also be synthesized from anhydrous creatine using esterification methods and isolated as their hydrochloride salts. For example, creatine ethyl ester hydrochloride may be synthesized by treatment of anhydrous creatine with ethanolic HCl at room temperature. See Dox., A. W.; Yoder, L. *Esterification of Creatine*. J. Biol. Chem., 67, 671-673, (1922) which is herein incorporated by reference in its entirety.

Using this method, creatine ethyl ester hydrochloride was synthesized in 74% yield after a single recrystallization from ethanol.

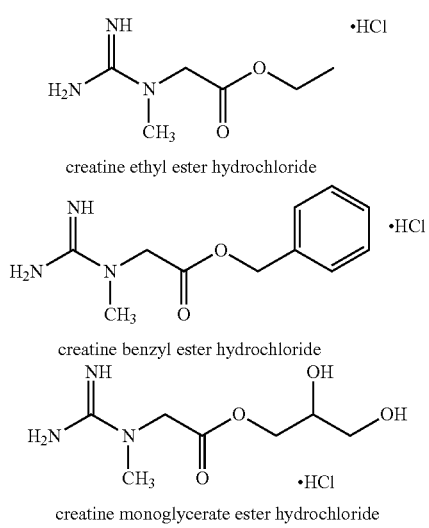

creatine ethyl ester hydrochloride creatine benzyl ester hydrochloride creatine monoglycerate ester hydrochloride Creatine ester compounds creatine benzyl ester hydrochloride and creatine monoglycerate ester hydrochloride may similarly be obtained by exposure of anhydrous creatine with excess HCl-saturated benzyl alcohol and glycerol, respectively. It is understood that stereoisomers, such as tereoisomers of creatine monoglycerate ester hydrochloride, and the compounds shown in FIGS. 28, 2E, 2F, 2G, 2J and the like, are also contemplated by the present invention.

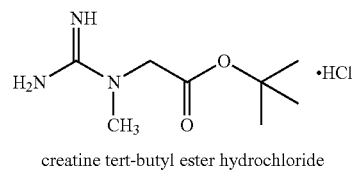

creatine tert-butyl ester hydrochloride

Creatine tert-butyl ester hydrochloride may be obtained by treatment of creatine acid chloride with tert-butanol and zinc chloride. See Rak, J.; Lubkowski, J.; Nikel, 1.; Przubulski, J.; Blazejowski, J. *Thermal Properties, Crystal Lattice Energy, Mechanism and Energetics of the Thermal Decomposition of Hydrochlorides of 2-Amino Acid Esters*, Thermochimica Acta 171, 253-277 (1990); Yadav, J. S.; Reddy, G. S.; Srinivas, D.; Himabindu, K. *Zinc Promoted Mild and Efficient Method for the Esterification of Acid Chlorides with Alcohols*, Synthetic Comm. 28, 2337-2342 (1998). Creatine tert-butyl ester hydrochloride may also be obtained by treatment of anhydrous creatine with tert-butanol and anhydrous magnesium sulfate and catalytic sulfuric acid. See Wright, S. W.; Hageman, D. L.; Wright, A. S.; McClure, L. D. *Convenient Preparations of t-Butyl Esters and Ethers from t-Butanol*, Tetrahedron Lett. 38, 7345-7348 (1997), which are herein incorporated by reference in their entireties.

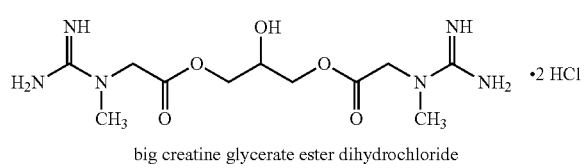 [SMILES: CN(CC(=O)OCC(O)COC(=O)CN(C)C(=N)N)C(=N)N ; "·2 HCl"]

big creatine glycerate ester dihydrochloride

His creatine glycerate ester dihydrochloride may be obtained by treatment of creatine acid chloride with a half-molar equivalent of anhydrous glycerol. See Rak, J.; Lubkowski, J.; Nikel, I.; Przubulski, J.; Blazejowski, J. *Thermal Properties, Crystal Lattice Energy, Mechanism and Energetics of the Thermal Decomposition of Hydrochlorides of 2-Amino Acid Ester*, Thermochimica Acta 71, 253-277 (1990), which is herein incorporated by reference in its entirety.

Alternatives to these methods include transesterification reaction of CE 1 using either catalytic diphenyl ammonium triflate and trimethylsilyl chloride (Wakasugi et al., 2000) or catalytic potassium tert-butoxide and 1 equivalent of tert-butyl acetate. Creatine acid chloride may also be used rather than anhydrous creatine in the esterification reactions. See Wakasugi, K.; Misake, T; Yamada, K.; Tanabe, Y. *Diphenylammonium triflate (DPAT): Efficient Catalyst for Esterification of Carboxylic Acids and For Transesterification of Carboxylic Esters With Nearly Equimolar Amounts of Alcohols*, Tetrahedron Lett. 41, 5249-5252 (2000), which is herein incorporated by reference in its entirety.

Regioselectivity problems in the formation of creatine esters, such as creatine monoglycerate ester hydrochloride, bis creatine glycerate ester dihydrochloride, and the like, may be addressed by selective esterification of the primary alcohol functional group(s) of glycerol with creatine acid chloride in the presence of N,N-diisopropylethylamine or 2,4,6-collidine at low temperatures. See Ishihara, K.; Kurihara, H.; Yamamoto, H. *An Extremely Simple, Convenient, and Selective Method for Acetylating Primary Alcohols in the Presence of Secondary Alcohols,* 1. Org Chem. 58, 3791-3793 (1993), which is herein incorporated by reference in its entirety.

Creatine esters may be purified by crystallization, flash column chromatography, and the like, if desired, and the structures and purity confirmed by analytical HPLC, $^1$H and $^{13}$C NMR, IR, melting point and elemental analysis. The following data was obtained through nuclear magnetic resonance spectroscopy of the corresponding compounds:

Creatine Ethyl Ester Hydrochloride $^1$H NMR (500 MHz, CDCl$_3$) δ1.12 (dq, J=6.0 Hz, J=1.0 Hz, 3H), 2.91, (s, 3H), 4.10-4.11 (m, 4H).

Creatine Benzyl Ester Hydrochloride $^1$H NMR (500 MHz, DMSO-d$_6$) (5 3.03 (s, 3H), 4.13 (s, 2H), 5.06 (s, 2H), 7.22-7.38 (m, 5H).

Clinical experience has shown that the intake of creatine ester, in particular a creatine ethyl ester (CEE) compound, may alleviate the inflammatory response triggered by physical or chemical injury of cellular tissue. Through investigation of the present invention it was found that creatine ester appears to function at a point, within the inflammatory response, prior to the activation of lipid peroxide species (precursors to arachidonic acids) by cyclooxygenase. Thus, the synthesis of cellular mediators (i.e., prostaglandins) that are important components in inflammatory responses and the resulting pain and discomfort experienced, is inhibited. Further, it has been shown that the creatine from the creatine ester compound does not inhibit either form of cyclooxygenase (COX I or COX 2) which is the main target of other anti-inflammatory agents such as the non-steroidal anti-inflammatory agents.

In an exemplary study primary cultured brain microvessel endothelial cells (BMEC) were used as an in vitro cell culture model to examine inflammation. These cells have been used previously to examine the effects of the intlammatory mediators such as tumor necrosis factor (TNF), and bacterial lipopolysaccharide (LPS). See Mark, K. S. and Miller, D. W. *increased Permeability of Prim my Cultured Brain Microvessel Endothelial Cell Monolayers Following Tumor Necrosis Factor-Alpha Exposure.* Life Sci. 64: 1941-1953, 1999, which is herein incorporated by reference in its entirety. See also Mark, K. S., Trickier, W. J., and Miller, D. W. *Role of Cyclooxygenase-2 and Prostaglandins in the TNF-a Induced Changes in Brain Microvessel Endothelial Cell Permeability.* J. Pharmacol. Exp. Ther. 297: I 051-1058, 200 I, which is herein incorporated by reference in its entirety. See also McGuire, T. R., Hoie, E., Trickier, W. F., Vranna, A., and Miller, D. W. *Release of Prostaglandin E-2 in Bovine Brain Endothelial Cells After Exposure to Three Unique Forms of the Antifungal Drug Amphotericin: Role of COX-2 in Amphotericin-Induced Fever.* Life Sci. (accepted for publication), which is herein incorporated by reference in its entirety. These studies indicate that following exposure to either tumor necrosis factor (TNF) or bacterial lipopolysaccharide (LPS), there is an increased expression of cyclooxygenase 2 (COX 2). This results in increased production and release of prostaglandins from the cells that is in turn associated with increased permeability of the brain microvessel endothelial cells (BMEC).

In the present study, the release of prostaglandin E2 (PGE2) from confluent monolayers of brain microvessel endothelial cells (BMEC) exposed to bacterial lipopolysaccharide (LPS) (20 ng/ml) either alone, or in the presence of various concentrations of creatine ethyl ester (CEE) hydrochloride salt (FIG. 6), or creatine monohydrate (CM) (FIG. 7), was examined. Treatment with bacterial lipopolysaccharide (LPS) alone caused significant increases in prostaglandin E2 (PGE2) release from the cells over the 12 hour exposure period (approximately 1a-fold increase over control). Co-administration of creatine ethyl ester (CEE) hydrochloride significantly reduced the amount of prostaglandin E2 (PGE2) released following bacterial lipopolysaccharide (LPS) exposure (FIG. 6). Reductions in prostaglandin E2 (PGE2) release were observed with creatine ethyl ester (CEE) hydrochloride concentrations as low as 10 µM. Maximal reductions in prostaglandin E2 (PGE2) release following bacterial lipopolysaccharide (LPS) exposure was observed with 100 µM of creatine ethyl ester (CEE) hydrochloride (FIG. 6). In contrast, with creatine monohydrate (CM), significant reductions in prostaglandin E2 (PGE2) release from the cells following bacterial lipopolysaccharide (LPS) exposure were not apparent until 100 µM, with maximal inhibitory responses requiring at least 1000 µM of creatine monohydrate (CM) (FIG. 7). By way of comparison, the magnitude of response observed with creatine ethyl ester (CEE) (100 µM) and creatine monohydrate (CM) (1000 µM), was similar to that observed with the anti-inflammatory agent, indomethacin (10 µM).

Additionally, the anti-inflammatory effects of creatine ethyl ester (CEE) on LPS-induced increases in brain microvessel endothelial cells (BMEC) monolayer permeability were examined. Confluent mono layers of brain microvessel endothelial cells (BMEC) were exposed to bacterial lipopolysaccharide (LPS) (20 ng/ml) for four hours, after which, permeability studies were performed using the fluorescent marker, fluorescein (FIG. 8). Exposure of brain microvessel endothelial cells (BMEC) monolayers to bacterial lipopolysaccharide (LPS) resulted in approximately 5-fold increases fluorescein permeability. Co-administration of 100 µM of either the creatine ethyl ester hydrochloride salt or the creatine ethyl ester bisulfate salt (CS04) resulted in significant reductions in the leakiness of the brain microvessel endothelial cell (BMEC) monolayers following bacterial lipopolysaccharide (LPS) exposure (FIG. 8). In contrast, 100 µM of creatine monohydrate (CM) had no effect on LPS-mediated increases in brain microvessel endothelial cells (BMEC) permeability (FIG. 8).

The studies described provide evidence for the anti-inflammatory actions of creatine ester compounds/pronutrients. The proof of principle was demonstrated with the creatine ethyl ester (CEE) derivative. While the ability to block/inhibit the release of prostaglandins following inflammatory stimuli is not unique to the creatine ester pronutrient compounds, as it also occurs with creatine monohydrate (CM), the creatine ester pronutrients appear to be more potent than the creatine monohydrate (CM) form. As the creatine ester compounds were designed to have better cell penetration and tissue accumulation than the standard forms of creatine currently on the market, the increased potency of creatine ethyl ester (CEE) in the anti-inflammatory assay is most likely due to better entry into the endothelial cells. The clinical ramifications of the increased potency of creatine ethyl ester (CEE) is that the concentrations required for inhibiting inflammation may be achieved, while those required for creatine monohydrate (CM) are well beyond the circulating plasma concentrations observed following creatine monohydrate (CM) nutritional supplementation. We anticipate that other ester pronutrient compounds such as those identified in our prior Patent Application Serial No.

PCT/USO1/28788 will have similar responses. Our studies show that at least two different salt forms of creatine ethyl ester (CEE) behave similarly in the inflammatory assays.

FIG. 9 shows a schematic of the arachidonic acid metabolite cascade that results in the formation of inflammatory mediators including prostaglandins, thromboxanes and luekotrienes. Our studies examining the ability of creatine ethyl ester (CEE) and creatine monohydrate (CM) to directly inhibit cyclooxygenase 1 or 2, have not presently revealed an inhibition of the enzyme at concentrations used in the current study. Thus, unlike many of the current non-steroidal anti-inflammatory drugs, creatine does not appear to inhibit the enzyme that converts prostacyclin into the various prostaglandins. As a result of the current investigations it appears that creatine works upstream in this pathway to prevent the formation of reactive lipid species that are precursors to arachidonic acid. This may be due to direct anti-oxidant activity of the molecule, or more likely, the importance of creatine in maintaining proper mitochondrial oxidative metabolism.

Referring now to FIG. 10, an exemplary embodiment of the present invention is illustrated showing the regulation of the inflammatory response in a cell. A biologically inactive creatine ester anti-inflammatory compound is introduced into a system in step 1010. The creatine ester anti-inflammatory compound delivers biologically active creatine to a cell which is undergoing an inflammatory response in step 1020. The metabolizing of the creatine ester compound into creatine may occur through an esterase cleaving the creatine from the ester as shown in FIG. IB. However, it is understood that alternate methods of producing biologically active creatine may be employed. In step 1030 the biologically active creatine increases its concentration in the mitochondria of the cell. Through clinical experience it has been shown that oxidative metabolism takes place within the mitochondria of the cell, this process being responsible for the regulation of free radical oxides, such as lipid peroxides, and the like, within the cell. Investigation of the present invention reveals that increased concentrations of creatine within the mitochondria of a cell may facilitate and/or maintain the oxidative metabolic activities of the mitochondria as indicated in step 1040, wherein the creatine is acting as an antioxidant. This anti-oxidant behavior may be responsible for suppression of the inflammatory response by significantly inhibiting and/or preventing the production of lipid peroxides. The decrease in lipid peroxide production in turn results in a diminished inflammatory response in the cell.

Delivery of the creatine ester may preferably occur through ingestion. It is contemplated that the creatine ester anti-inflammatory compound may be formulated as an aqueous solution, such as a liquid drink, and allow for oral ingestion. Further, the creatine ester anti-inflammatory compound may be formulated as an organic compound including all solid oral formulations, such as granules, a tablet, a capsule, and the like, for ingestion. Alternatively, a food supplement, such as a sports bar, and the like, may be employed for delivery of the creatine ester anti-inflammatory compound.

The solid oral formulation of the creatine ester anti-inflammatory compound may further include a controlled release formulation. This may enhance the anti-inflammatory capabilities by enabling an anti-inflammation response over a prolonged period of time. Thus, the creatine ester anti-inflammatory compound may be useful during activities (i.e., athletic events) which may initiate the inflammatory response in cells.

Other formulations, such as an emulsion, suspension, and the like, may be employed and allow delivery of the present invention to a desired location. The formulations may allow application through a variety of methods, such as a topical application, parenteral application, and the like. For example, topical creatine ester anti-inflammatory compounds may include ointments, lotions, creams, gels, controlled release systems such as adhesive patches for prolonged topical applications, controlled release wraps for prolonged topical applications to larger muscle areas, and the like, and may be applied directly to an inflamed area. In exemplary embodiments, the transdermal patches and wraps are formulated to contain the creatine ester anti-inflammatory compounds in an internal semi-solid reservoir surrounded on one side with a semi-permeable membrane for diffusion-controlled release onto intact skin. To prepare other medicated topical formulations, creatine ester forms may be dissolved or dispersed within a lipoidal liquid or semi-solid vehicle that is then impregnated or adsorbed into the wraps and patches. In the current embodiments, release is controlled by partitioning or dissolution of the creatine ester anti-inflammatory compounds. Such a local application may potentiate the effects of oral administration of a creatine compound. These organic compounds may further comprise penetrating agents, which may be employed to increase the bio-availability of the creatine ester across a membrane, enhancing the topical creatine ester compound lipophilicity. For example, lipophilic solvents and/or nonionic surfactants may be used to further promote absorption. It is contemplated that the creatine ester employed, via the topical delivery vehicle, may include a controlled release formulation similar to that described previously for the solid oral formulation. Other methods used to facilitate transdermal absorption of these creatine derivatives include iontophoresis and sonophoresis which may be employed with or without the inclusion of penetration enhancing agents.

A topical formulation of the creatine ethyl ester (CEE), of the present invention, may be prepared within a preferred range of 15-25% (w/w) creatine ethyl ester in a 20% microemulsion of Pluronic-lecithin organogel (PLO). In a first exemplary formulation of the present invention, a preparation of 17.5% CEE in PLO may be prepared by adding 80 mls of 20% Poloxamer base to a past containing 20 grams of CEE; said CEE paste is made by using 20 mls of preserved lecithin Isopropyl Palmitate. In a second exemplary formulation, a preparation of 22.5% CEE in PLO maybe be prepared by adding 80 mls of 20% poloxamer to a paste containing 25% grams of CEE; again the CEE paste is made by using 20 mls of preserved lecithin Isopropyl Palmitate. In a third exemplary formulation, a preparation of 22.5% CEE in PLO (29.6 gm in 131.5 gm total mass), may be prepared by adding 80 mls of 20% Poloxamer to a paste of CEE; again the CEE paste is made by using 20 mls of preserved lecithin Isopropyl Palmitate. In a forth exemplary formulation, a preparation of 22.8% CEE in PLO (29.5 gm in 129.1 gm total mass), may be prepared by adding 80 mls of 20% Poloxamer to a paste of CEE; again the CEE paste is made by using 20 mls of preserved lecithin Isopropyl Palmitate. In a fifth exemplary formulation, a preparation of 23% CEE in PLO (31.9 gm in 138.5 gm total mass), may be be prepared by adding 80 mls of 20% Poloxamer base to a paste of CEE; said CEE paste is made by using 20 mls of preserved lecithin Isopropyl Palmitate. In a sixth exemplary formulation, a preparation of 23% CEE in PLO (30.0 gm in 130.5 gm total mass), maybe be prepared by adding 80 mls of 20% Poloxamer base to a paste of CEE; said CEE paste is made by using 20 mls of preserved lecithin Isopropyl Palmitate. In a seventh exemplary formulation, a preparation of 25% CEE in PLO (28 gm in 114 gm total volume), maybe be prepared by adding 80 mls of 20% Poloxamer base to a paste containing 25 grams of CEE; said CEE paste is made by using 20 mls of preserved lecithin Isopropyl Palmitate. In an eighth exemplary formulation, a preparation of 25% CEE in PLO (29 gm in 115 gm total volume), may be be prepared by adding 80 mls of 20% Poloxamer base to a paste containing 29 grams of CEE; said CEE paste is made by using 20 mls of preserved lecithin Isopropyl Palmitate. The ester form (CEE) may be incorporated in either the lipid phase (lecithin isopropyl palmitate or lecithin isopropyl myristate) or the aqueous phase (pluronic) in a 20% to 80% volume to volume proportion of the lipid to aqueous phases. The result is an internal droplet diameter suitable for percutaneous absorption of the CEE and other ester forms of creatine via both transepidermal and transfollicular pathways. The lipophilic nature of the creatine ester formulations, such as CEE, in PLO enhances the transdermal absorption of creatine and its direct delivery to strained, inflamed, or injured muscles and tendons. Thus, topical applications, such as those being described herein, may facilitate muscle recovery, reduction in muscle pain from stress and/or cramping due to lactic acid production in muscle, and reduced inflammation in muscles and tendons.

Such topical formulations as described above may be delivered in an ointment or included in the patch and/or wrap delivery vehicle for local application. Further, it is understood that alternative formulations of the creatine esters, suitable as an ointment or for inclusion in the patch and/or wrap delivery vehicle system, may include organic solutions like dimethysulfoxide (DSMO) or short chain, water insoluble higher molecular weight alcohols, esters, and glycols. The suspensions may be provided in an aqueous vehicle and liposome structured vehicles. As described above, organogels may be prepared from bentonite or veegum (inorganic). The ointment vehicles may include hydrophobic hydrocarbon vehicles (mineral oil, paraffins); anhydrous or hydrous lanolins, oil/water emulsions (hydrophilic ointment), or water soluble vehicles, such as PEG (Percutaneous Entreal Gastrostomy) ointments, without departing from the scope and spirit of the present invention.

Parenteral methods of delivering the anti-inflammatory creatine ester compound may include injections (subcutaneous, intramuscular, or intravenous), suppositories (rectal or vaginal), and the like. Injections may comprise sterile solutions containing the creatine ester anti-inflammatory compound and may be delivered directly to the bloodstream or deposited in the inflamed tissue itself. The suppositories may contain suspensions, solids, or liquid formulations of the creatine ester anti-inflammatory.

FIG. 11 illustrates an exemplary embodiment of the present invention, showing the various stages of the inflammatory response of a tissue or cell. Additionally, FIG. 11 shows, that the creatine from the creatine ester anti-inflammatory compound may interrupt this inflammatory cascade at a variety of stages to prevent the formation of inflammatory chemical mediators. In a preferred embodiment, the creatine is concentrated in the mitochondria of an inflamed cell or tissue and interrupts the inflammatory cascade prior to the generation of lipid peroxides (i.e., arachidonic acid). The interruption involves an improvement in the mitochondrial metabolic capacity resulting in the production of fewer lipid peroxides and ultimately, fewer chemical mediators of inflammation (i.e., prostaglandins). Thus, the creatine is acting as an antioxidant within the inflamed cell or tissue.

Alternatively, the inflammatory cascade may be interrupted by the anti-oxidative activity of the creatine within the cell or tissue immediately following the physical or chemical damaging activity, after the blood cells have released the first wave of chemical mediators, or after the peptide proteins have been produced, activated, and released from the adjacent nerves, nerve endings, or clotting factors in the blood. It is understood that the inflammatory response shown in FIG. 11 is a simplified version of the inflammatory response and that those or ordinary skill in the art may include various changes within the process. Further, it is contemplated that the creatine, from the creatine ester anti-inflammatory compound of the present invention, may interrupt the inflammatory response at a variety of stages without departing from the scope and spirit of the present invention.

Referring now to FIG. 12, further evidence of the increased bio-availability of creatine provided to target cells and tissue through use of the creatine ester compounds of the present invention, is shown. In this study, the accumulation of creatine in C2C12 Muscle Cells (mouse skeletal muscle cell line) was examined. As evidence through the graphic presentation of FIG. 12, the cells were exposed to creatine monohydrate (CM) or creatine ethyl ester (CEE), in amounts of 3.2 mg/ml, for up to 1 hour at 37 C. Over this time period it was observed that here is a significant, approximately two-fold, increase in the "loading" of CEE in the muscle cells versus CM loading. FIGS. 13 through 15 exemplify the effects of this increased loading of CEE in the C2C12 cells under normal and hypoxic conditions. FIGS. 13 through 15 illustrate the results of studies of lactic acid levels in and lactic acid release from C2C12 muscle cells. The treatment group consisted of control cells receiving no exposure to creatine of any form, creatine monohydrate (CM) cells being exposed to 100 uM of CM, or creatine ethyl ester (CEE) cells being exposed to 100 uM of CEE. The results were gathered over a six hour period of time. As exemplified by the FIGS. 13 through 15, the cells treated with CEE show a marked reduction in lactic acid levels and release. This may be attributed to the increased "loading" or bio-availability of creatine in cells exposed to the CEE compound of the present invention.

It is understood that the specific order or hierarchy of steps in the methods disclosed are examples of exemplary approaches. Based upon design preferences, it is understood that the specific order or hierarchy of steps in the method may be arranged while remaining within the scope and spirit of the present invention. The accompanying method claims present elements of the various steps in a sample order, and are not necessarily meant to be limited to the specific order hierarchy presented.

It is believed that the creatine ester anti-inflammatory compounds and formulations of the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof. It is the intention of the following claims to encompass and include such changes.

What is claimed is:

1. A method of delivering an anti-inflammatory compound to an inflamed target tissue of an animal, comprising:
   administering to the skin of the animal a topical formulation comprising an anti-inflammatory agent that is present in an amount effective to achieve plasma concentrations sufficient to increase creatine concentration at the target tissue, wherein the amount of anti-inflammatory agent in the topical formulation is about 15 percent to about 25 percent by weight, and wherein the anti-inflammatory agent comprises a creatine ethyl ester, a creatine ethyl ester salt, or a combination thereof.

2. The method as described in claim 1, wherein the creatine ethyl ester and/or creatine ethyl ester salt is administered to the animal, the creatine ester is modified by the animal into creatine and an alcohol.

3. The method as described in claim 2, wherein the creatine ethyl ester and/or creatine ethyl ester salt is modified by the animal into creatine and alcohol by an esterase.

4. The method as described in claim 3, wherein the creatine ethyl ester and/or creatine ethyl ester salt is modified by at least one of an intestinal lumen, epithelial cell and blood of the animal into creatine.

5. The method as described in claim 1, further comprising forming a creatine ethyl ester and/or creatine ethyl ester salt, wherein an acid moiety of creatine is modified to provide an ester bond.

6. The method as described in claim 1, wherein the animal includes a human and livestock.

7. The method as described in claim 1, further comprising metabolizing the creatine ethyl ester and/or creatine ethyl ester salt within a mitochondria to down regulate lipid peroxide availability.

8. A method of delivering an anti-inflammatory compound to an inflamed target tissue of an animal, comprising:
administering to the skin of the animal an effective amount of a topical anti-inflammatory formulation consisting essentially of (a) at least one of a creatine ethyl ester and a creatine ethyl ester salt, the creatine ethyl ester and/or creatine ethyl ester salt being modified by the animal to form creatine and (b) a penetrating agent, wherein the creatine ethyl ester and/or creatine ethyl ester salt is present in the topical anti-inflammatory formulation in an amount of about 15 percent to about 25 percent by weight.

9. The method of claim 1, wherein the topical anti-inflammatory formulation is administered to the animal in the form of an ointment, a cream, a patch, or a wrap delivery vehicle.

10. The method of claim 8, wherein the topical anti-inflammatory formulation is administered to the animal in the form of an ointment, a cream, a patch, or a wrap delivery vehicle.

11. The method of claim 8, wherein the creatine ethyl ester and/or creatine ethyl ester salt is administered to the animal, the creatine ester is modified by the animal into creatine and an alcohol.

12. The method of claim 8, wherein the creatine ethyl ester and/or creatine ethyl ester salt is modified by at least one of an intestinal lumen, epithelial cell and blood of the animal into creatine.

13. The method of claim 8, wherein the animal includes a human and livestock.

14. A method of delivering an anti-inflammatory compound to an inflamed target tissue of an animal, comprising:
applying a topical anti-inflammatory formulation to the skin of the animal, wherein the topical anti-inflammatory formulation comprises creatine ethyl ester in an amount of about 15 percent to about 25 percent by weight, the creatine ethyl ester being modified by the animal to form creatine.

15. The method of claim 14, wherein the topical application is applied to the animal in the form of an ointment, a cream, a patch, or a wrap delivery vehicle.

16. The method of claim 14, wherein the animal includes a human and livestock.

17. The method of claim 14, wherein the creatine ethyl ester is administered to the animal, the creatine ester is modified by the animal into creatine and an alcohol.

18. The method of claim 8, wherein the penetrating agent is a microemulsion of Pluronic-lecithin organogel (PLO).

* * * * *